(12) United States Patent
Kondou et al.

(10) Patent No.: US 11,203,024 B2
(45) Date of Patent: Dec. 21, 2021

(54) LIQUID ATOMIZATION DEVICE AND AIR CLEANER USING SAME

(71) Applicant: Panasonic Intellectual Property Management Co., Ltd., Osaka (JP)

(72) Inventors: Hiroyuki Kondou, Aichi (JP); Masahide Fukumoto, Aichi (JP); Yoshiya Shigenobu, Aichi (JP); Masato Honda, Aichi (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/975,349

(22) PCT Filed: Feb. 15, 2019

(86) PCT No.: PCT/JP2019/005543
§ 371 (c)(1),
(2) Date: Aug. 24, 2020

(87) PCT Pub. No.: WO2019/167667
PCT Pub. Date: Sep. 6, 2019

(65) Prior Publication Data
US 2020/0391232 A1 Dec. 17, 2020

(30) Foreign Application Priority Data

Feb. 28, 2018 (JP) .............................. JP2018-034114
Feb. 28, 2018 (JP) .............................. JP2018-034115
(Continued)

(51) Int. Cl.
*A61L 9/14* (2006.01)
*B05B 3/10* (2006.01)
(Continued)

(52) U.S. Cl.
CPC .............. *B05B 3/1021* (2013.01); *A61L 9/14* (2013.01); *B05B 3/1064* (2013.01);
(Continued)

(58) Field of Classification Search
CPC ........ A61L 9/14; A61L 9/145; A61L 2101/20; A61L 2209/134; A61L 2209/16; B05B 3/1021; B05B 3/1064
See application file for complete search history.

(56) References Cited

FOREIGN PATENT DOCUMENTS

| JP | H09-155139 A | 6/1997 |
|---|---|---|
| JP | 2009-095390 A | 5/2009 |

(Continued)

OTHER PUBLICATIONS

International Search Report issued in corresponding International Patent Application No. PCT/JP2019/005543, dated Apr. 16, 2019, English translation.

*Primary Examiner* — Timothy C Cleveland
(74) *Attorney, Agent, or Firm* — McDermott Will & Emery LLP

(57) ABSTRACT

A liquid atomization device includes: an inlet; an outlet; and a liquid atomization chamber. The liquid atomization chamber is provided in an air passage between the inlet and the outlet. The liquid atomization chamber includes a rotary shaft, a pumping pipe, a collision wall, a reservoir, and a drain port. The rotary shaft is rotated by a rotary motor and is disposed in the vertical direction. The pumping pipe includes a lower portion having a pumping port and an upper portion fixed to the rotary shaft, and is rotated in coordination with rotation of the rotary shaft to pump up water through the pumping port and centrifugally discharge the water. The pumping pipe generates, inside the pumping pipe, a whirlpool in the water in the reservoir by the rotation, and forms, at the center of the whirlpool, a void providing (Continued)

communication between the pumping port and the drain port.

14 Claims, 14 Drawing Sheets

(30) Foreign Application Priority Data

Aug. 29, 2018 (JP) .............................. JP2018-159823
Sep. 21, 2018 (JP) .............................. JP2018-176751

(51) Int. Cl.
  *A61L 101/20* (2006.01)
  *F24F 6/16* (2006.01)
(52) U.S. Cl.
  CPC ..... *A61L 2101/20* (2020.08); *A61L 2209/134* (2013.01); *A61L 2209/16* (2013.01); *F24F 6/16* (2013.01)

(56) References Cited

FOREIGN PATENT DOCUMENTS

| | | | |
|---|---|---|---|
| JP | 2009-279514 | A | 12/2009 |
| JP | 2010-142595 | A | 7/2010 |
| JP | 2011-012860 | A | 1/2011 |
| JP | 2016-041210 | A | 3/2016 |

LIQUID ATOMIZATION DEVICE AND AIR CLEANER USING SAME

CROSS-REFERENCE OF RELATED APPLICATIONS

This application is the U.S. National Phase under 35 U.S.C. § 371 of International Patent Application No. PCT/JP2019/005543, filed on Feb. 15, 2019, which in turn claims the benefit of Japanese Patent Application No. 2018-034114, filed Feb. 28, 2018; Japanese Patent Application No. 2018-034115, filed Feb. 28, 2018; Japanese Patent Application No. 2018-159823, filed Aug. 29, 2018; and Japanese Patent Application No. 2018-176751, filed Sep. 21, 2018, the entire disclosures of which Applications are incorporated by reference herein.

TECHNICAL FIELD

The present disclosure relates to liquid atomization devices.

BACKGROUND ART

Conventionally, there is a liquid atomization device that atomizes water, mixes the atomized water into drawn-in air, and forces the air out (for example, Patent Literature (PTL) 1). In such a liquid atomization device, a liquid atomization chamber for atomizing water is provided in an air passage between an inlet through which air is drawn in and an outlet through which the drawn-in air is forced out. The liquid atomization chamber includes a pumping pipe fixed to a rotary shaft of a rotary motor. The rotary motor causes the pumping pipe to rotate and thus allows the pumping pipe to pump up water stored in a reservoir and centrifugally discharge the water that has been pumped up. The discharged water hits a collision wall, resulting in water atomization.

Furthermore, in the conventional liquid atomization device, a drain pipe for draining water stored in the reservoir after the operation ends is connected to the bottom surface of the reservoir. The drain pipe includes a drain valve; the drain valve is closed while the liquid atomization device is in operation, but, after the liquid atomization device stops operating, the drain valve opens to drain the water stored in the reservoir.

CITATION LIST

Patent Literature

PTL 1: Unexamined Japanese Patent Publication No. 2009-279514

SUMMARY OF THE INVENTION

In the conventional liquid atomization device, however, since a water stop mechanism for the drain pipe is small, a gap in the drain valve through which water can flow is narrow, causing the problem that a drain mechanism is easily clogged with foreign matter contained in water.

The present disclosure has been conceived to solve the aforementioned problem and has an object to provide a liquid atomization device including a drain mechanism that is less likely to be clogged, and a heat exchange ventilation device, an air cleaner, and an air conditioner that use the liquid atomization device.

In order to achieve the above object, a liquid atomization device according to one aspect of the present disclosure includes: an inlet through which air is drawn in; an outlet through which the air drawn in through the inlet is forced out; and a liquid atomization chamber. The liquid atomization chamber is provided in an air passage between the inlet and the outlet, and water is atomized in the liquid atomization chamber. The liquid atomization chamber includes a rotary shaft, a pumping pipe, a collision wall, a reservoir, and a drain port. The rotary shaft is rotated by a rotary motor and is disposed in a vertical direction. The pumping pipe has a tubular shape, includes a lower portion having a pumping port and an upper portion fixed to the rotary shaft, and is rotated in coordination with the rotation of the rotary shaft to pump up water through the pumping port and centrifugally discharge the water that has been pumped up. The water discharged by the pumping pipe hits the collision wall to cause atomization of the water. The reservoir is provided vertically below the pumping pipe and stores the water to be pumped up by the pumping pipe through the pumping port. The drain port is provided on the bottom surface of the reservoir, and the water that has been stored is drained through the drain port. The pumping pipe generates, inside the pumping pipe, a whirlpool in the water in the reservoir by the rotation of the pumping pipe, and forms, at the center of the whirlpool, a void providing communication between the pumping port and the drain port.

Furthermore, a heat exchange ventilation device, an air cleaner, and an air conditioner according to the present disclosure incorporate the liquid atomization device described above.

In the liquid atomization device according to the present disclosure and the heat exchange ventilation device, the air cleaner, and the air conditioner according to the present disclosure that use the liquid atomization device, the rotation of the pumping pipe that is performed to atomize water generates, inside the pumping pipe, a whirlpool in the water in the reservoir and forms, at the center of the whirlpool, a void providing communication between the pumping port and the drain port. With this, the drainage of the water in the reservoir through the drain port can be inhibited while the liquid atomization device is in operation. On the other hand, when the pumping pipe stops rotating, the water in the reservoir flows into the drain port. Thus, when the liquid atomization device stops operating, the water in the reservoir can be drained. In this manner, even without the use of a drain valve in a drain mechanism, it is possible to inhibit the drainage of the water in a reservoir through a drain port during operation and drain the water in the reservoir through the drain port after the operation stops. This produces the advantageous effects of eliminating the need for a drain valve and providing a drain mechanism that is less likely to be clogged.

DESCRIPTION OF EMBODIMENTS

Hereinafter, exemplary embodiments of the present disclosure will be described with reference to the accompanying drawings. Note that each of the exemplary embodiments described below shows one specific preferred example of the present disclosure. Therefore, the numerical values, shapes, materials, structural elements, the arrangement and connection of the structural elements, etc., shown in the following exemplary embodiments are mere examples, and are not intended to limit the present disclosure. As such, among the structural elements in the following exemplary embodiments, structural elements not recited in any one of the independent claims which indicate the broadest concepts of the present disclosure are described as arbitrary structural elements. Furthermore, in the respective figures, substantially identical elements are assigned the same reference marks, and overlapping description is omitted or simplified.

First Exemplary Embodiment

Figure 1:
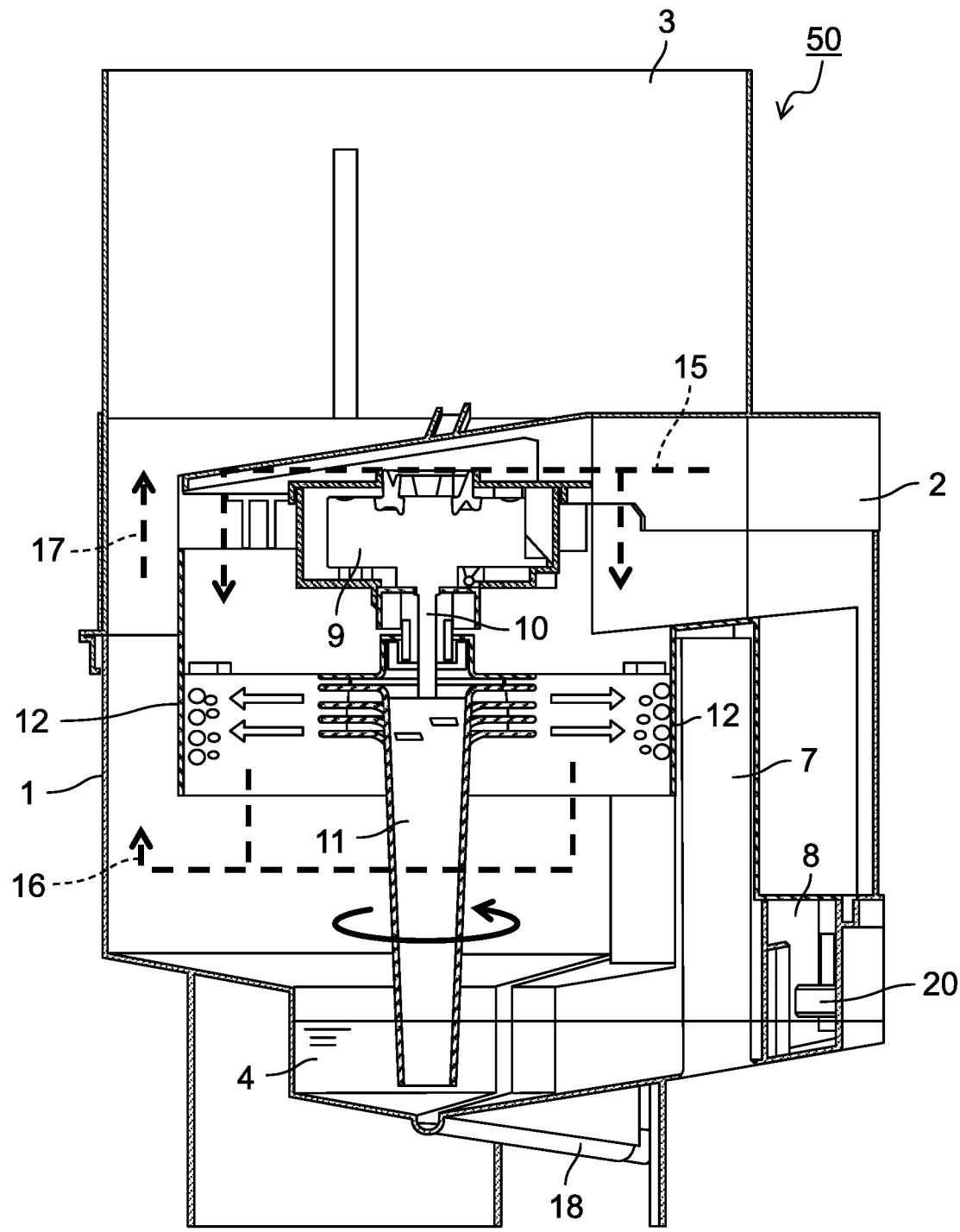
FIG. 1 is a schematic vertical cross-sectional view of a liquid atomization device according to the first exemplary embodiment of the present disclosure.
Figure 2:
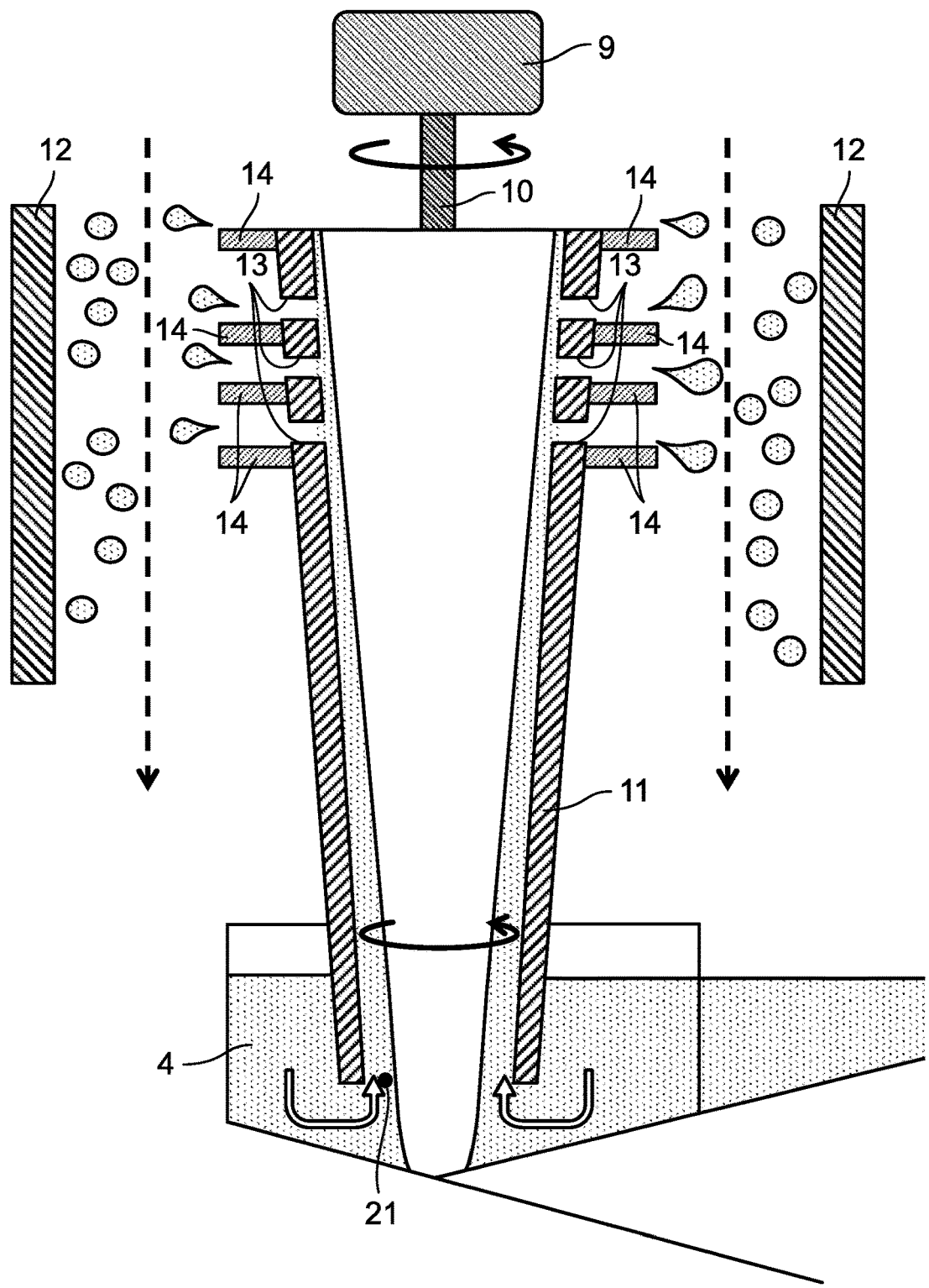
FIG. 2 is a diagram for illustrating the operating principles of the liquid atomization device.

First, the schematic configuration of liquid atomization device 50 according to the first exemplary embodiment of the present disclosure will be described with reference to FIG. 1 and FIG. 2. FIG. 1 is a schematic vertical cross-sectional view of liquid atomization device 50 according to the first exemplary embodiment. FIG. 2 is a diagram for illustrating the operating principles of liquid atomization device 50 according to the first exemplary embodiment.

Liquid atomization device 50 includes: inlet 2 through which air is drawn in; outlet 3 through which the air drawn in through inlet 2 is forced out; and liquid atomization chamber 1. In liquid atomization device 50, air passages 15 to 17 are formed between inlet 2 and outlet 3. Furthermore, liquid atomization chamber 1 is provided in air passages 15 to 17, and inlet 2, liquid atomization chamber 1, and outlet 3 are in communication with one another.

Liquid atomization chamber 1, which is a main part of liquid atomization device 50, is where water is atomized. In liquid atomization device 50, the air drawn in through inlet 2 is delivered to liquid atomization chamber 1 via air passage 15. Liquid atomization device 50 is configured to mix, into air passing through air passage 16, the water atomized in liquid atomization chamber 1 and force out the air mixed with the water through outlet 3 via air passage 17.

In liquid atomization chamber 1, collision wall 12 open at the top and bottom is provided. Collision wall 12 is fixed inside liquid atomization chamber 1. Furthermore, liquid atomization chamber 1 includes, in the inner area surrounded by collision wall 12, tubular pumping pipe 11 which rotates to draw up (pump up) water. Pumping pipe 11 has a hollow structure in the shape of an inverted cone and includes circular pumping port 21 (refer to FIG. 2) at the bottom, and rotary shaft 10 is fixed at the center of the base of the inverted cone above pumping pipe 11 in such a manner as to extend in the vertical direction. Rotary shaft 10 is connected to rotary motor 9 provided on the outer surface of liquid atomization chamber 1, and thus the rotary motion of rotary motor 9 is transmitted to pumping pipe 11 through rotary shaft 10, causing pumping pipe 11 to rotate.

As illustrated in FIG. 2, pumping pipe 11 includes a plurality of rotary plates 14 formed so as to protrude outward from the outer surface of pumping pipe 11. The plurality of rotary plates 14 are formed at predetermined intervals along the axis of rotary shaft 10 so as to protrude outward from the outer surface of pumping pipe 11. Rotary plate 14 rotates together with pumping pipe 11 and is therefore preferably in the shape of a horizontal disc that is coaxial with rotary shaft 10. Note that the total number of rotary plates 14 is set, as appropriate, depending on intended performance, the dimensions of pumping pipe 11, and so on.

Furthermore, the wall of pumping pipe 11 includes a plurality of openings 13 penetrating the wall of pumping pipe 11. Each of the plurality of openings 13 is positioned to provide communication between the inside of pumping pipe 11 and an upper surface of rotary plate 14 formed so as to protrude outward from the outer surface of pumping pipe 11. It is necessary to design each opening 13 by setting the size thereof in the circumferential direction (opening percentage) according to the outer diameter of a portion of pumping pipe 11 at which opening 13 is located. For example, it is sufficient that the size of opening 13 in the circumferential direction be set equivalent to 5% to 50% of the outer diameter of pumping pipe 11 and more preferably set equivalent to 5% to 20% of the outer diameter of pumping pipe 11. Note that the dimensions of respective openings 13 may be set equal to one another within this range.

As illustrated in FIG. 1, in a lower portion of liquid atomization chamber 1, reservoir 4 which stores the water to be pumped up by pumping pipe 11 through pumping port 21 is provided vertically below pumping pipe 11. Reservoir 4 is designed to have a depth such that a lower portion of pumping pipe 11 is partially soaked, for example, a portion the length of which is approximately one-third to one-hundredth of the height of the cone of pumping pipe 11 is soaked. The design for this depth can be adjusted according to a required amount of water to be pumped. The bottom surface of reservoir 4 is formed in the shape of a bowl projecting toward drain port 22 to be described later (refer to FIG. 3).

Water is supplied to reservoir 4 using water supply unit 7. A water supply pipe (not illustrated in the drawings) is connected to water supply unit 7 and, for example, water is directly supplied thereto from a water service line by the water supply pipe via a water pressure regulator valve. Note that water supply unit 7 may be configured to supply water to reservoir 4 by drawing up only the required amount of water from a water tank provided outside liquid atomization chamber 1 using the siphon principle in advance.

Water level sensor 8 that senses the level of water in reservoir 4 is provided in liquid atomization chamber 1. Water level sensor 8 includes float switch 20. When water in reservoir 4 has not reached a predetermined water level, float switch 20 is OFF, and when water in reservoir 4 reaches the predetermined water level, float switch 20 is turned ON. The predetermined water level is set so that a lower portion of pumping pipe 11 is soaked in the water stored in reservoir 4. When float switch 20 is OFF, water supply unit 7 supplies water to reservoir 4, and when float switch 20 is ON, the water supply from water supply unit 7 to reservoir 4 is stopped. This allows water in reservoir 4 to be maintained at a predetermined water level.

Drain pipe 18 is connected to the bottom surface of reservoir 4. Circular drain port 22 (refer to FIG. 3) provided at the position where drain pipe 18 is connected is located at the lowest point of the bottom surface of reservoir 4, which is formed in the shape of a bowl. The water stop and drainage by drain pipe 18 are achieved through the rotation of pumping pipe 11. In other words, drain pipe 18 and pumping pipe 11 constitute a water stop mechanism and a pumping mechanism for reservoir 4. Note that details of the water stop mechanism and the pumping mechanism for reservoir 4 using drain pipe 18 and pumping pipe 11 will be described later with reference to FIG. 3.

Here, the operating principles of water atomization in liquid atomization device 50 will be described. Rotary motor 9 causes rotary shaft 10 to rotate, pumping pipe 11 rotates accordingly, and centrifugal force generated by the rotation allows pumping pipe 11 to draw up the water stored in reservoir 4. The rotational speed of pumping pipe 11 is set to 1,000 to 5,000 rpm. Since pumping pipe 11 has a hollow structure in the shape of an inverted cone, the water drawn up by the rotation is pumped up to the upper portion by moving along the inner wall of pumping pipe 11. Subsequently, the water that has been pumped up is centrifugally discharged from opening 13 of pumping pipe 11 along rotary plate 14 and splashes as water droplets.

The water droplets splashed from rotary plate 14 travel in the space surrounded by collision wall 12, hit collision wall 12, and are thus atomized. Meanwhile, air passing through liquid atomization chamber 1 moves from the upper opening of collision wall 12 to the inside of collision wall 12, takes in water droplets disintegrated (atomized) by collision wall 12, and moves out of collision wall 12 through the lower opening of collision wall 12. Thus, liquid atomization device 50 can moisturize the air drawn in through inlet 2 and force out the moisturized air through outlet 3.

Since the kinetic energy of the water splashed from rotary plate 14 decays by friction against air inside collision wall 12, rotary plate 14 is preferably placed as close to collision wall 12 as possible. However, as the distance between collision wall 12 and rotary plate 14 is reduced, the amount of air passing through collision wall 12 is reduced; thus, the lower limit value of the distance between collision wall 12 and rotary plate 14 is arbitrarily determined according to the pressure loss and the amount of air passing through collision wall 12.

Note that the liquid to be atomized may be other than water; for example, a liquid such as antibacterial or deodorant hypochlorous acid water may be used. The atomized hypochlorous acid water is mixed into the air drawn in through inlet 2 of liquid atomization device 50, and then the air is forced out through outlet 3; thus, space in which liquid atomization device 50 is placed can be sterilized or deodorized.

Figure 3:
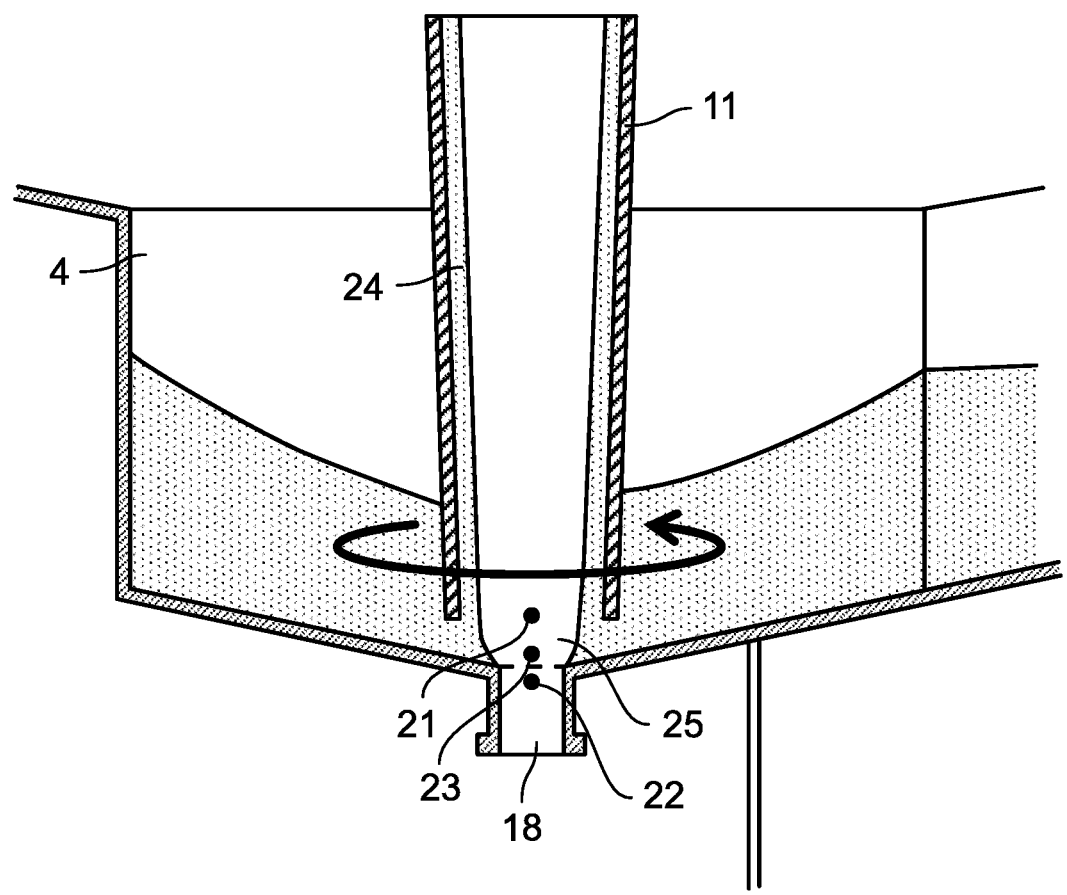
FIG. 3 is a diagram for illustrating a water stop mechanism for a reservoir using a drain pipe and a pumping pipe in the liquid atomization device.

Next, with reference to FIG. 3, details of the water stop mechanism and the pumping mechanism for reservoir 4 using drain pipe 18 and pumping pipe 11 will be described. FIG. 3 is a diagram for illustrating the water stop mechanism for reservoir 4 using drain pipe 18 and pumping pipe 11.

When pumping pipe 11 is rotated while liquid atomization device 50 is in operation, the centrifugal force of the rotation generates, inside pumping pipe 11, whirlpool 24 in the water in reservoir 4. Furthermore, pumping pipe 11 forms void 25 between whirlpool center bottom 23 generated by the rotation and drain port 22 to which drain pipe 18 is connected. In other words, pumping pipe 11 generates, inside pumping pipe 11, whirlpool 24 in the water in reservoir 4 by the rotation, and forms, at the center of whirlpool 24, void 25 providing communication between pumping port 21 and drain port 22. With this, the drainage of the water in reservoir 4 through drain port 22 can be inhibited while liquid atomization device 50 is in operation.

On the other hand, when pumping pipe 11 stops rotating, the water in reservoir 4 flows into drain port 22. Thus, when liquid atomization device 50 stops operating, the water in reservoir 4 can be drained through drain port 22.

In this manner, even without the use of a drain valve in drain pipe 18, it is possible to inhibit (stop) the drainage of the water in reservoir 4 through drain port 22 during operation of liquid atomization device 50 and drain the water in reservoir 4 through drain port 22 after the operation stops. Therefore, liquid atomization device 50 can eliminate the need for a drain valve. As a result, the area of drain port 22 and the diameter of drain pipe 18 can be made larger, for example, and thus it is possible to provide a drain mechanism that is less likely to be clogged.

Furthermore, in the present exemplary embodiment, the bottom surface of reservoir 4 is formed in the shape of a bowl projecting toward drain port 22. This makes it easy to give centrifugal force to the water stored in reservoir 4 when pumping pipe 11 is rotated. Accordingly, whirlpool 24 can be more easily generated in the water in reservoir 4 inside pumping pipe 11, and generated whirlpool 24 can be stably maintained. Furthermore, when pumping pipe 11 stops rotating, the water stored in reservoir 4 can be reliably drained through drain port 22.

Figure 4A:
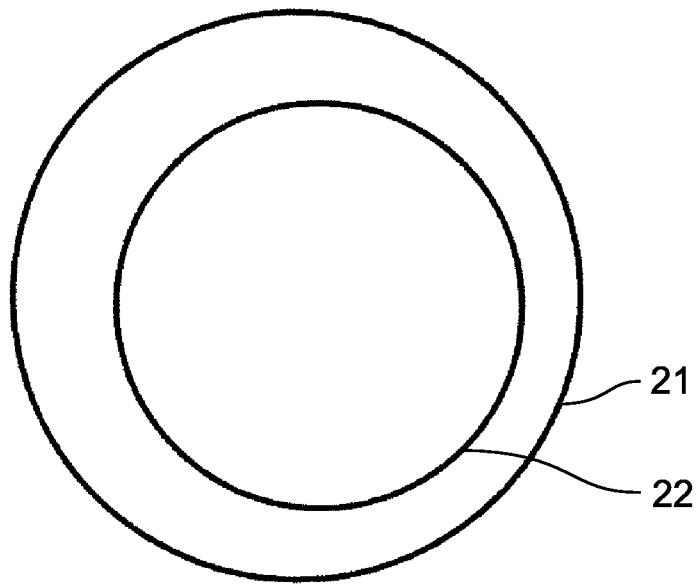
FIG. 4A is a diagram illustrating the positional relationship between a pumping port and a drain port in the liquid atomization device.
Figure 4B:
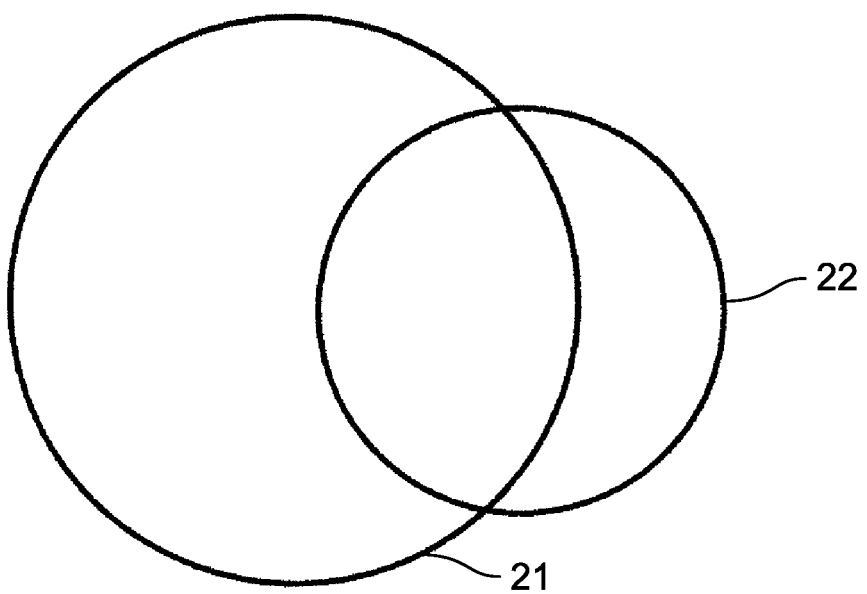
FIG. 4B is a diagram illustrating the positional relationship between the pumping port and the drain port in the liquid atomization device.

Now, with reference to FIG. 4A and FIG. 4B, the positional relationship between pumping port 21 and drain port 22 of pumping pipe 11 will be described. FIG. 4A and FIG. 4B are diagrams illustrating the positional relationship between pumping port 21 and drain port 22 in liquid atomization device 50 according to the first exemplary embodiment. Note that FIG. 4A is a schematic view illustrating one example of the positional relationship between pumping port 21 and drain port 22 in liquid atomization device 50 according to the first exemplary embodiment when pumping pipe 11 is viewed from above in the vertical direction. FIG. 4B is a schematic view illustrating another example of the positional relationship.

In the example illustrated in FIG. 4A, drain port 22 is disposed inward of pumping port 21. This makes it possible to generate whirlpool 24 in reservoir 4 by the rotation of pumping pipe 11 and easily form, at the center of whirlpool 24, void 25 providing communication between pumping port 21 and drain port 22. Therefore, the drainage through drain port 22 can be certainly stopped while liquid atomization device 50 is in operation. Note that although FIG. 4A illustrates the case where the center of the circle of pumping port 21 and the center of the circle of drain port 22 are offset when pumping pipe 11 is viewed from above in the vertical direction, it is further preferred that the center of the circle of pumping port 21 and the center of the circle of drain port 22 are aligned, in other words, pumping port 21 and drain port 22 are concentrically arranged.

Furthermore, as in another example illustrated in FIG. 4B, pumping port 21 and drain port 22 may be arranged so as to overlap each other. In this case, in reservoir 4, void 25 can be formed at least between pumping port 21 and a portion of drain port 22 by the rotation of pumping pipe 11. Thus, while liquid atomization device 50 is in operation, complete water stoppage is not possible, but void 25 formed above drain port 22 makes it possible to reduce the amount of water that is drained through drain port 22.

In order to form void 25 between whirlpool center bottom 23 generated by the rotation of pumping pipe 11 and drain port 22 to which drain pipe 18 is connected, the larger the diameter of pumping port 21 is relative to the diameter of drain port 22, the better. For example, suppose that the diameter of drain port 22 is 1, the diameter of pumping port 21 is preferably set to 1.3 or more. As the diameter of pumping port 21 increases, the size of void 25 that is generated inside pumping pipe 11 in reservoir 4 by the rotation of pumping pipe 11 increases, and void 25 can be more easily formed between pumping port 21 and drain port 22.

Furthermore, in order to form void 25 between whirlpool center bottom 23 generated by the rotation of pumping pipe 11 and drain port 22 to which drain pipe 18 is connected, the larger the area of pumping port 21 is relative to the area of drain port 22, the better. In other words, the larger the area of pumping port 21 is relative to the area of drain port 22, the better, to form void 25 providing communication between pumping port 21 and drain port 22 at the center of whirlpool 24. For example, suppose that the area of drain port 22 is 1, the area of pumping port 21 is preferably set to 1.7 or more. As the area of pumping port 21 increases, the size of void 25 that is generated inside pumping pipe 11 in reservoir 4 by the rotation of pumping pipe 11 increases, and void 25 can be more easily formed between pumping port 21 and drain port 22.

Note that the shape of drain port 22 does not necessarily need to be circular and may be polygonal.

Figure 5:
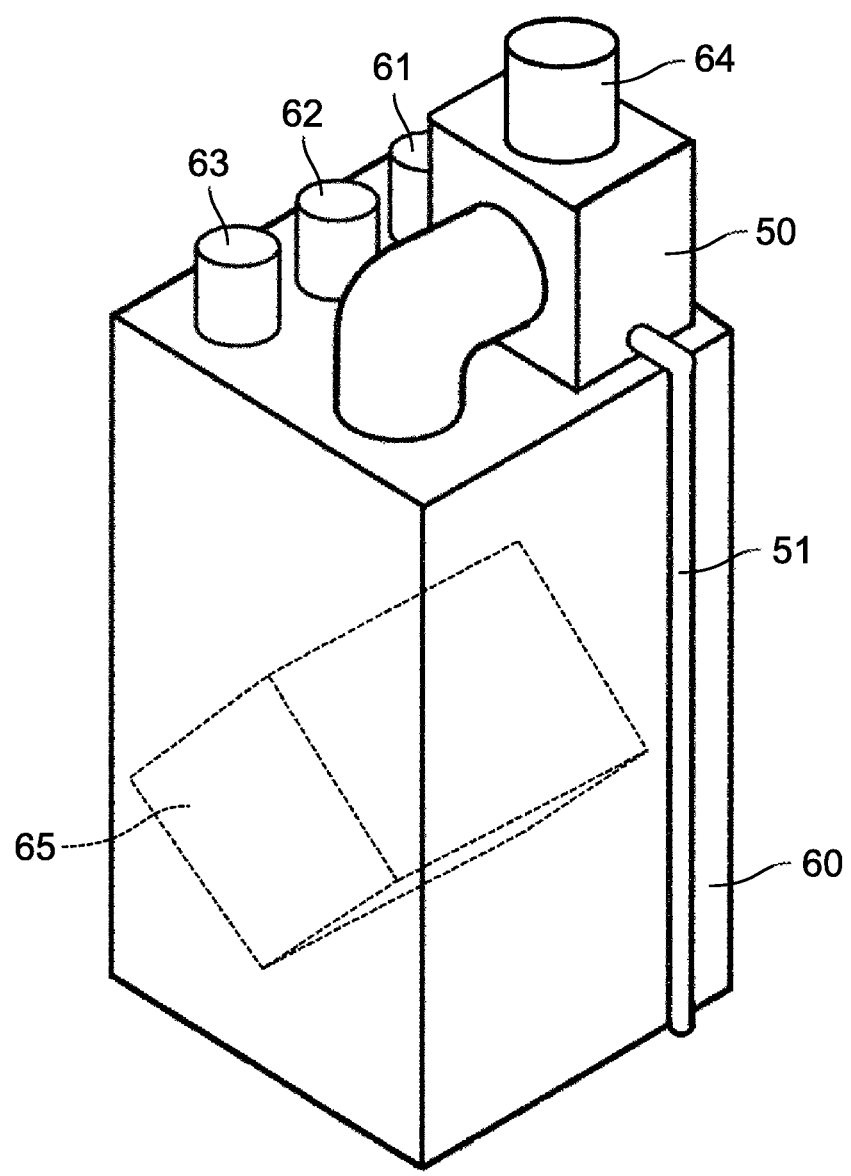
FIG. 5 is a schematic perspective view of a heat exchange ventilation device incorporating the liquid atomization device.

FIG. 5 is a schematic perspective view of heat exchange ventilation device 60 incorporating liquid atomization device 50 according to the first exemplary embodiment of the present disclosure. Heat exchange ventilation device 60 includes: indoor inlet 61 and air intake port 64 that are provided in a room of a building; exhaust port 62 and outside air inlet 63 that are provided outside the building; and heat exchange element 65 provided in a main body.

Air inside the room is drawn in through indoor inlet 61, and the drawn-in air is discharged to the outside through exhaust port 62. Outside air outside the room is drawn in through outside air inlet 63, and the drawn-in outside air is supplied into the room through air intake port 64. At this time, heat exchange element 65 exchanges heat between the air delivered from indoor inlet 61 to exhaust port 62 and the outside air delivered from outside air inlet 63 to air intake port 64.

Some heat exchange ventilation devices incorporate, as one function, a device that vaporizes a liquid such as a water vaporization device intended to be used to increase humidity and a hypochlorous acid vaporization device intended to be used for sterilization or deodorization. Heat exchange ventilation device 60 incorporates liquid atomization device 50 as the device that vaporizes a liquid. Specifically, liquid atomization device 50 is provided on the air intake port 64 side of heat exchange ventilation device 60. Note that water supply/drain pipe 51 is used to supply water to and drain water from liquid atomization device 50.

Heat exchange ventilation device 60 incorporating liquid atomization device 50 mixes, into outside air that has been subjected to the heat exchange of heat exchange element 65, water or hypochlorous acid water atomized by liquid atomization device 50, and supplies the resultant air into the room through air intake port 64. By using liquid atomization device 50 as a mechanism for vaporizing the liquid, it is possible to obtain miniaturized heat exchange ventilation device 60 with improved energy efficiency.

Liquid atomization device 50 may be provided in an air cleaner or an air conditioner instead of heat exchange ventilation device 60. Some air cleaners or air conditioners incorporate, as one function, a device that vaporizes a liquid such as a water vaporization device intended to be used to increase humidity and a hypochlorous acid vaporization device intended to be used for sterilization or deodorization. By using liquid atomization device 50 as this device, it is possible to obtain a miniaturized air cleaner or air conditioner with improved energy efficiency.

Second Exemplary Embodiment

The difference between a liquid atomization device according to the second exemplary embodiment and the liquid atomization device according to the first exemplary embodiment is the structure of pumping pipe 11 (specifically, the structure of a tip portion of pumping pipe 11) for generating whirlpool 24 in the water in reservoir 4 by the rotation and forming, at the center of whirlpool 24, void 25 providing communication between pumping port 21 and drain port 22 to stop water. The configuration of liquid atomization device 50 other than the structure of the tip portion of pumping pipe 11 is substantially the same as that in the first exemplary embodiment (FIG. 1 and FIG. 2). Hereinafter, explanation of the content described in the first exemplary embodiment will be omitted, as appropriate, and the points of difference from the first exemplary embodiment will be mainly explained.

Figure 6:
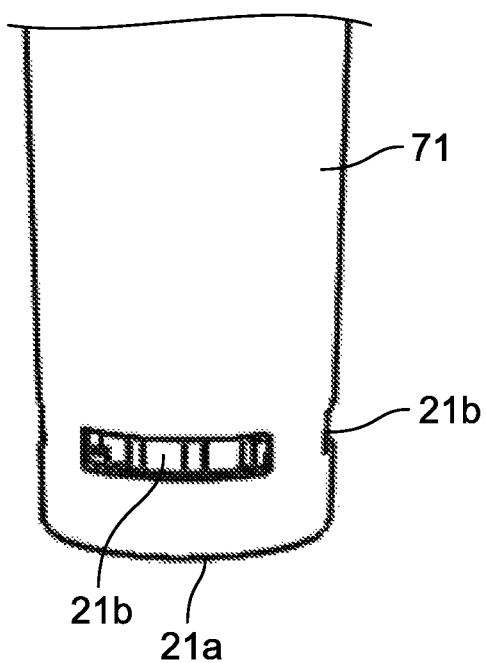
FIG. 6 is a schematic perspective view of a tip portion of a pumping pipe in a liquid atomization device according to the second exemplary embodiment of the present disclosure.

With reference to FIG. 6 to FIG. 9, the schematic configuration of a tip portion of pumping pipe 71 in liquid atomization device 50 according to the second exemplary embodiment of the present disclosure will be described. FIG. 6 is a schematic perspective view of the tip portion of pumping pipe 71 in the liquid atomization device according to the second exemplary embodiment. FIG. 7A and FIG. 7B are cross-sectional views of the tip portion of pumping pipe 71 in the liquid atomization device according to the second exemplary embodiment. Note that FIG. 7A is a diagram of pumping pipe 71 when viewed from obliquely above and FIG. 7B is a diagram of pumping pipe 71 when viewed from the side. FIG. 8A is a cross-sectional view taken along line A-A' in FIG. 7B. FIG. 8B is a cross-sectional view taken along line B-B' in FIG. 7B.

As illustrated in FIG. 6, pumping pipe 71 of liquid atomization device 50 according to the second exemplary embodiment includes, as pumping ports for drawing up water in reservoir 4 during rotation, first pumping port 21a located at the tip portion of pumping pipe 71 and second pumping port 21b located above first pumping port 21a. Note that second pumping port 21b is not only located above first pumping port 21a, but also formed in pumping pipe 71, above a position at which rib parts 26 (refer to FIG. 7A and FIG. 7B) to be described later are formed.

First pumping port 21a, which corresponds to pumping port 21 according to the first exemplary embodiment, is formed in a circle by reflecting the hollow structure in the shape of an inverted cone of pumping pipe 71.

Figure 8A:
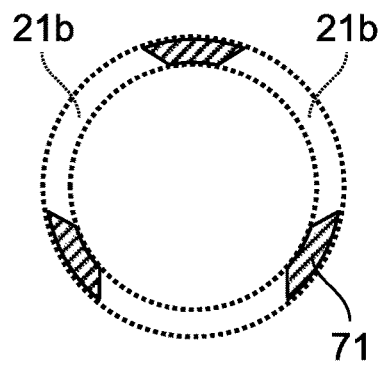
FIG. 8A is a cross-sectional view taken along line A-A' in FIG. 7B.

Second pumping port 21b, which is a square opening, is formed in a wall of pumping pipe 71 in such a manner as to penetrate the wall. A plurality of second pumping ports 21b are formed along the circumference of the wall of pumping pipe 71. In the present exemplary embodiment, as illustrated in FIG. 8A, three second pumping ports 21b having the same shape are formed along the circumference of pumping pipe 71. Note that the total area of the openings along the circumference of second pumping port 21b is set in consideration of the pumping ability of first pumping port 21a (the amount of water to be pumped up through first pumping port 21a) and the pumping ability of second pumping port 21b (the amount of water to be pumped up through second pumping port 21b).

Figure 7A:
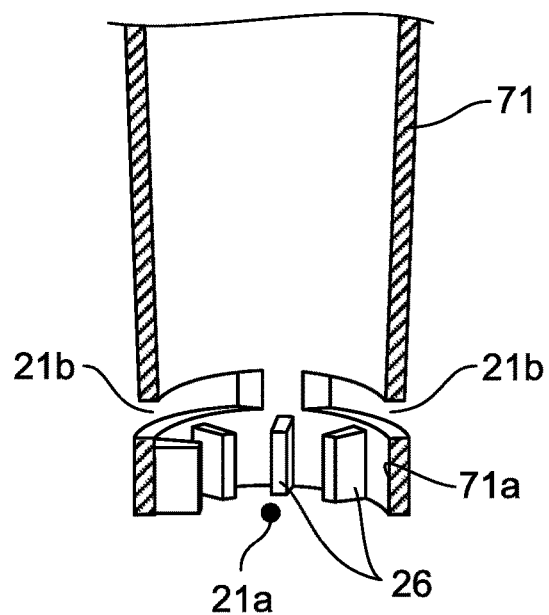
FIG. 7A is a cross-sectional view of the tip portion of the pumping pipe in the liquid atomization device.
Figure 7B:
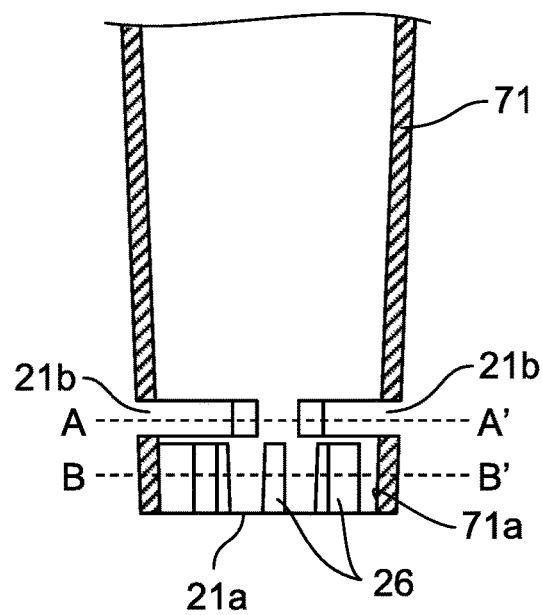
FIG. 7B is a cross-sectional view of the tip portion of the pumping pipe in the liquid atomization device.
Figure 8B:
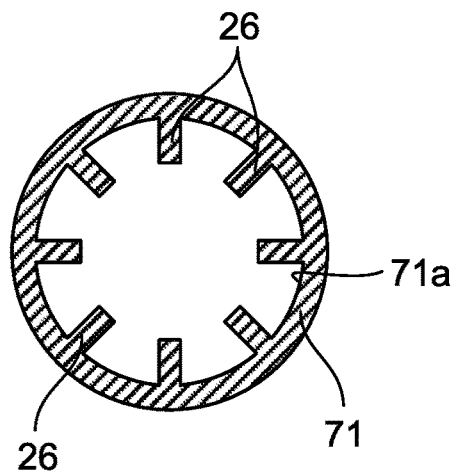
FIG. 8B is a cross-sectional view taken along line B-B' in FIG. 7B.

As illustrated in FIG. 7A and FIG. 7B, on pumping pipe 71, a plurality of rib parts 26 are formed on a wall surface between first pumping port 21a and second pumping port 21b (on the inner wall 71a side). Rib part 26 has a columnar shape and is formed so as to protrude from inner wall 71a of pumping pipe 71 toward the center of pumping pipe 71. The plurality of rib parts 26 are formed along the circumference of inner wall 71a of pumping pipe 71. In the present exemplary embodiment, as illustrated in FIG. 8B, eight rib parts 26 having the same shape are formed along the circumference of inner wall 71a. Note that the size, shape, number, positions, etc., of rib parts 26 are set in consideration of the water stop ability of pumping pipe 71.

Figure 9:
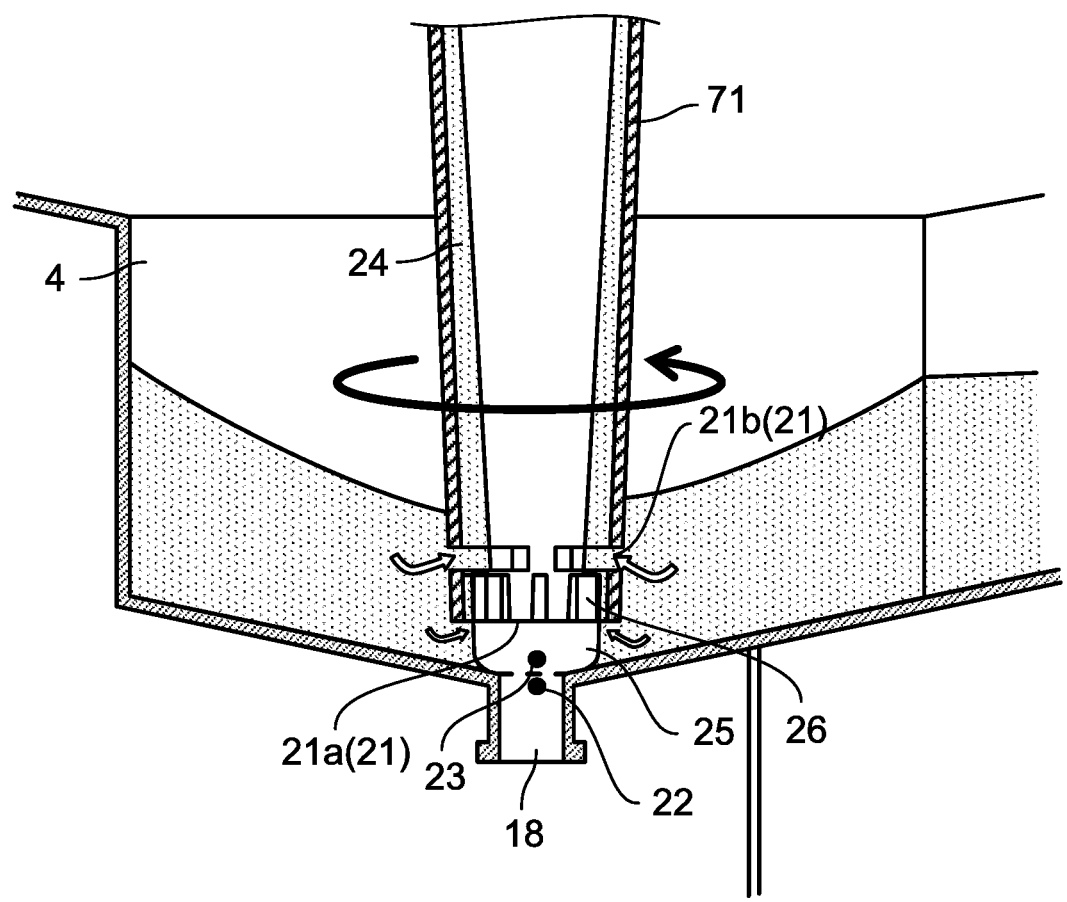
FIG. 9 is a diagram for illustrating a water stop mechanism for a reservoir using a drain pipe and a pumping pipe in the liquid atomization device according to the second exemplary embodiment of the present disclosure.

Next, with reference to FIG. 9, details of the water stop mechanism for reservoir 4 using drain pipe 18 and pumping pipe 71 in liquid atomization device 50 according to the second exemplary embodiment will be described. FIG. 9 is a diagram for illustrating the water stop mechanism for reservoir 4 using drain pipe 18 and pumping pipe 71 in liquid atomization device 50.

As described in the first exemplary embodiment, when pumping pipe 71 is rotated while liquid atomization device 50 is in operation, the centrifugal force of the rotation generates, inside pumping pipe 71, whirlpool 24 in the water in reservoir 4. Furthermore, pumping pipe 71 forms, at the center of whirlpool 24, void 25 providing communication between pumping port 21 and drain port 22 to which drain pipe 18 is connected. With this, the drainage of the water in reservoir 4 through drain port 22 can be inhibited while liquid atomization device 50 is in operation (refer to FIG. 3).

In the present exemplary embodiment, as illustrated in FIG. 9, at the tip portion of pumping pipe 71, the plurality of rib parts 26 are formed along the circumference of inner wall 71a of pumping pipe 71. The plurality of rib parts 26 push water in corresponding regions by the rotation of pumping pipe 71 and easily give centrifugal force to the water in these regions, allowing whirlpool 24 to be easily generated in the water in these regions. In other words, assume that the rotation (rotational speed) of pumping pipe 71 is the same, whirlpool 24 that is generated by rib part 26 can be stronger. As a result, at the center of whirlpool 24 that is generated by the rotation, void 25 providing communication between pumping port 21 and drain port 22 to which drain pipe 18 is connected is reinforced, and thus force for reducing the amount of water that is drained through drain port 22 (water stop force) improves. In particular, the effects of the improvements on the water stop force are prominent when pumping pipe 71 operates at a low rotational speed (for example, between 1,000 and 2,000 rpm).

The operations after pumping pipe 71 stops rotating are substantially the same as those in the first exemplary embodiment and as such, descriptions thereof will be omitted.

Next, pumping up of pumping pipe 71 of liquid atomization device 50 according to the second exemplary embodiment will be described with reference to FIG. 9.

As described in the first exemplary embodiment, in liquid atomization device 50, rotary motor 9 causes rotary shaft 10 to rotate, pumping pipe 71 rotates accordingly, and centrifugal force generated by the rotation allows pumping pipe 71 to draw up the water stored in reservoir 4. Since pumping pipe 71 has a hollow structure in the shape of an inverted cone, the water drawn up through pumping port 21 of pumping pipe 71 by the rotation is pumped up to the upper portion by moving along the inner wall of pumping pipe 71 (refer to FIG. 2).

In the present exemplary embodiment, as illustrated in FIG. 9, pumping pipe 71 includes first pumping port 21a and second pumping port 21b as pumping ports. The water drawn up through each of first pumping port 21a and second pumping port 21b of pumping pipe 71 by the rotation is pumped up to the upper portion by moving along the inner wall of pumping pipe 71. In particular, since second pumping port 21b is provided above a region in which whirlpool 24 is created (regions in which first pumping port 21a and rib parts 26 are located), water can be easily introduced into pumping pipe 71 regardless of the flow rate of whirlpool 24 in the region. Furthermore, in the present exemplary embodiment, as compared to the pumping port according to the first exemplary embodiment, second pumping port 21b increases the total amount of water that is pumped up, enabling liquid atomization device 50 to operate stably.

Although FIG. 5 illustrates an example in which liquid atomization device 50 according to the first exemplary embodiment is applied to heat exchange ventilation device 60 incorporating a liquid atomization device, this is not limiting. For example, liquid atomization device 50 according to the second exemplary embodiment may be applied. With this, it is also possible to obtain miniaturized heat exchange ventilation device 60 with improved energy efficiency. It goes without saying that even by incorporating the liquid atomization device into an air cleaner or an air conditioner instead of heat exchange ventilation device 60, it is possible to obtain miniaturized air cleaner or air conditioner with improved energy efficiency.

In the second exemplary embodiment, columnar rib parts 26 are provided on inner wall 71a at the tip portion of pumping pipe 71 of liquid atomization device 50, but this is not limiting. It is sufficient that pumping pipe 71 be structured to push, by rotation thereof, water in the region, in the direction of the rotation (along the outer circumference); for example, a curved rib structure or a vertically multilayered (for example, two-layer) rib structure may be used. With this, the design flexibility for the water stop mechanism improves.

Third Exemplary Embodiment

Conventionally, there is a liquid atomization device that atomizes water, mixes the atomized water into drawn-in air, and forces the air out (for example, Patent Literature (PTL) 1). In such a liquid atomization device, a liquid atomization chamber for atomizing water is provided in an air passage between an inlet through which air is drawn in and an outlet through which the drawn-in air is forced out. The liquid atomization chamber includes a pumping pipe fixed to a rotary shaft of a rotary motor. The rotary motor causes the pumping pipe to rotate and thus allows the pumping pipe to pump up water stored in a reservoir and centrifugally discharge the water that has been pumped up. The discharged water hits a collision wall, resulting in water atomization.

Furthermore, in order to secure that a predetermined amount of water is stored in the reservoir during operation, the conventional liquid atomization device includes: a water supply unit which supplies water to the reservoir; and a water level sensor which senses the level of water in the reservoir.

However, in the conventional liquid atomization device, when the water supply unit supplies water to the reservoir, the supplied water temporarily moves to a position away from the water supply unit, and thus fluctuations such as a rise of a water surface occur depending on the position in the reservoir. This causes the problem of being unable to accurately sense a water level due to the water level sensor sensing a water level on the basis of the water surface after the fluctuation.

The present disclosure has an object to provide a liquid atomization device capable of accurately sensing the level of water in a reservoir, and a heat exchange ventilation device, an air cleaner, and an air conditioner that use the liquid atomization device.

In order to achieve the above object, a liquid atomization device according to another aspect of the present disclosure includes: an inlet through which air is drawn in; an outlet through which the air drawn in through the inlet is forced out; and a liquid atomization chamber which is provided in an air passage between the inlet and the outlet and in which water is atomized. The liquid atomization chamber includes a pumping pipe, a reservoir, a water supply unit, a first water channel, and a water level sensor. The pumping pipe has a tubular shape and is rotated to pump up water and centrifugally discharge the water that has been pumped up. The reservoir is provided vertically below the pumping pipe and stores the water to be pumped up by the pumping pipe. The water supply unit supplies water to the reservoir. The first water channel guides water from the water supply unit to the reservoir. The water level sensor senses the level of water in the reservoir. The water supply unit and the water level sensor are provided at positions vertically higher than the position of the bottom surface of the reservoir. In an area close to the reservoir, the first water channel is in communication with the water level sensor via a second water channel different from the first water channel. When water is supplied, the water flows from the reservoir toward the water level sensor into the second water channel.

Furthermore, a heat exchange ventilation device, an air cleaner, and an air conditioner according to the present disclosure incorporate the liquid atomization device described above.

In the liquid atomization device according to the present disclosure and the heat exchange ventilation device, the air cleaner, and the air conditioner that use the liquid atomization device, the water level sensor is closer to the water supply unit than to the reservoir. This makes it possible to reduce, at the water level sensor, the impact of a change in the level of the water surface that occurs when water is supplied. Thus, there is the advantage of being able to accurately sense the level of water in the reservoir.

Figure 10:
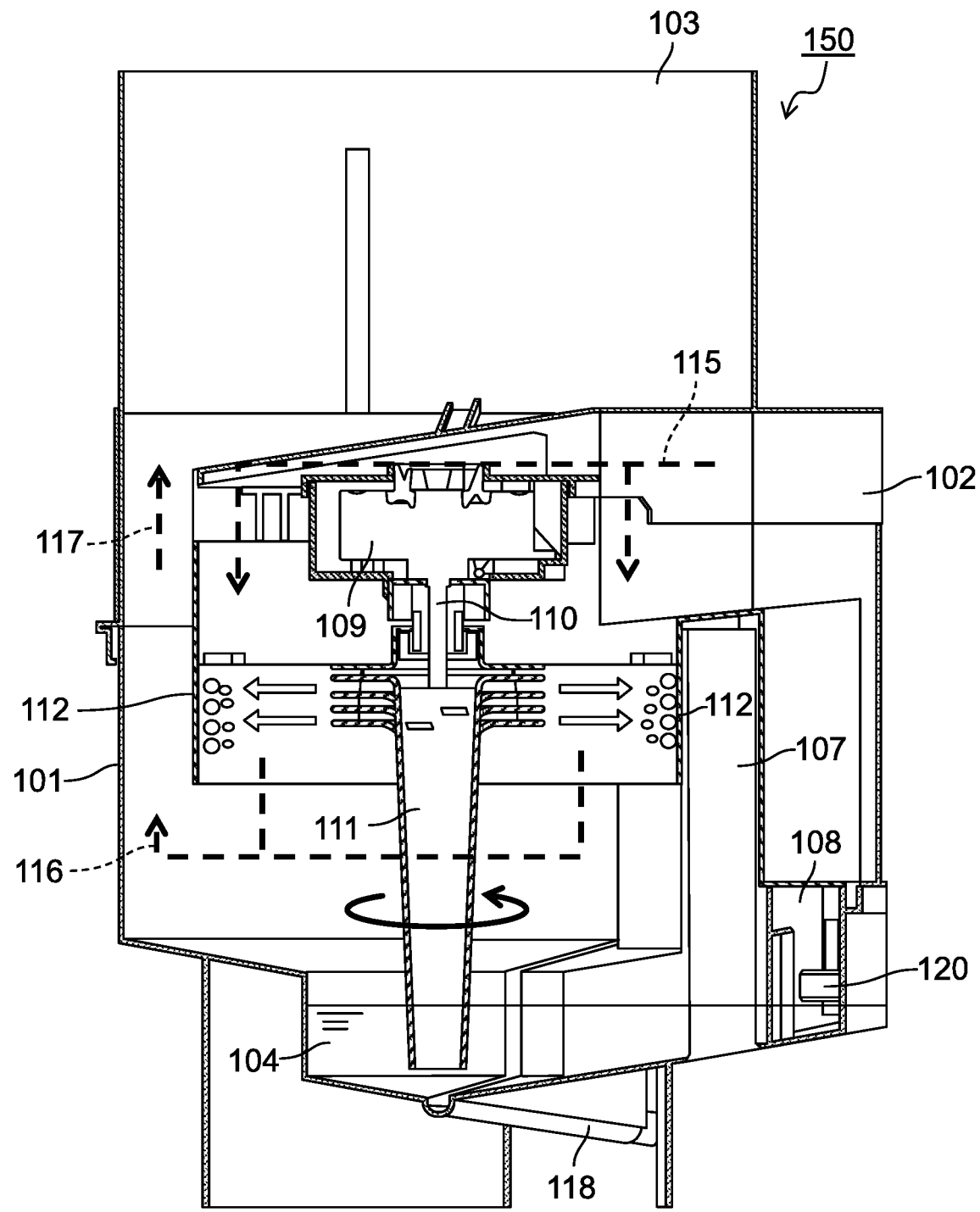
FIG. 10 is a schematic cross-sectional view of a liquid atomization device according to the third exemplary embodiment of the present disclosure.
Figure 11:
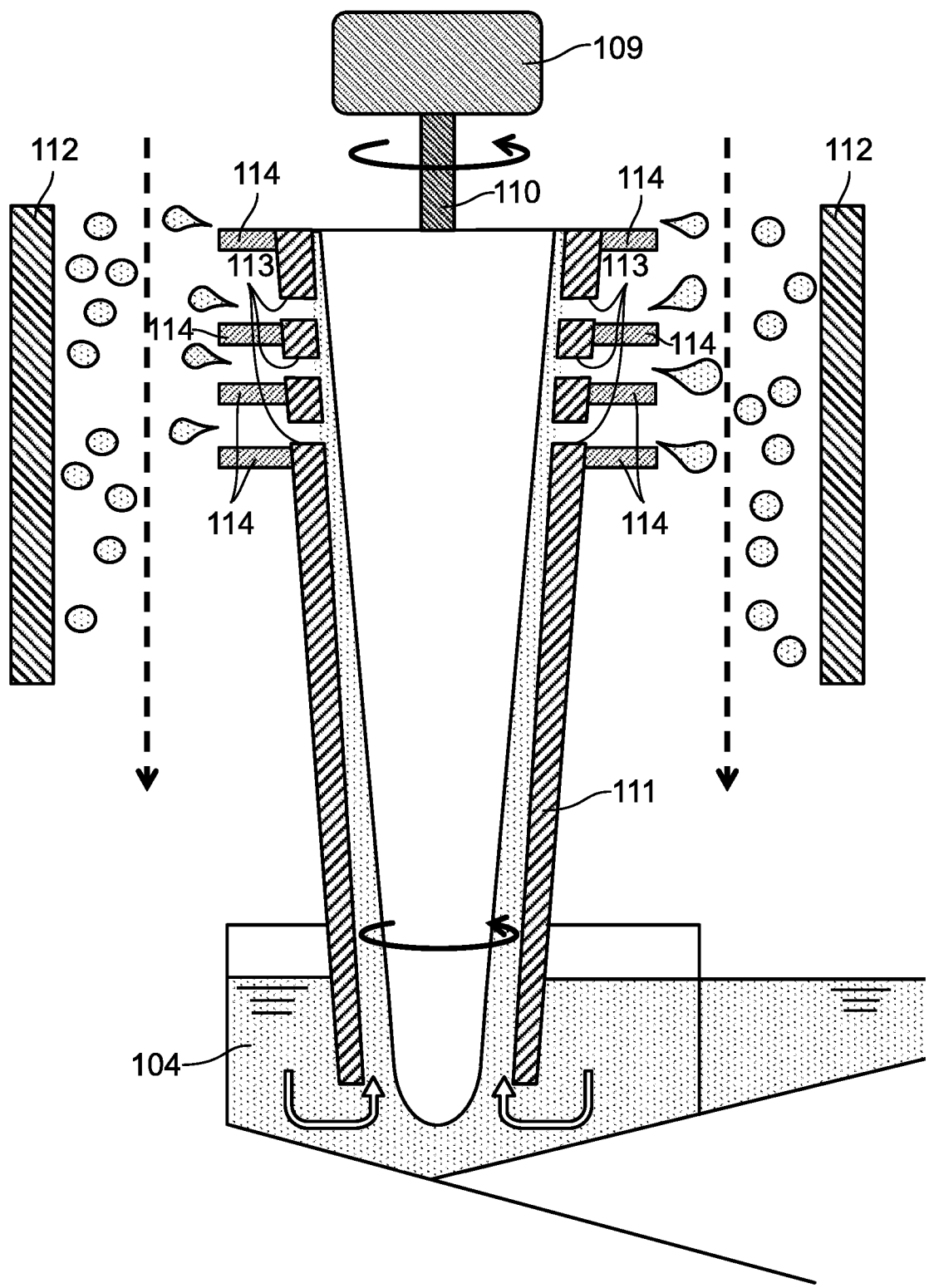
FIG. 11 is a diagram for illustrating the operating principles of the liquid atomization device.

First, the schematic configuration of liquid atomization device 150 according to the third exemplary embodiment of the present disclosure will be described with reference to FIG. 10 and FIG. 11. FIG. 10 is a schematic vertical cross-sectional view of liquid atomization device 150. FIG. 11 is a diagram for illustrating the operating principles of liquid atomization device 150.

Liquid atomization device 150 includes: inlet 102 through which air is drawn in; outlet 103 through which the air drawn in through inlet 102 is forced out; and liquid atomization chamber 101. In liquid atomization device 150, air passages 115 to 117 are formed between inlet 102 and outlet 103. Furthermore, liquid atomization chamber 101 is provided in air passages 115 to 117, and inlet 102, liquid atomization chamber 101, and outlet 103 are in communication with one another.

Liquid atomization chamber 101, which is a main part of liquid atomization device 150, is where water is atomized. In liquid atomization device 150, the air drawn in through inlet 102 is delivered to liquid atomization chamber 101 via air passage 115. Liquid atomization device 150 is configured to mix, into air passing through air passage 116, the water atomized in liquid atomization chamber 101 and force out the air mixed with the water through outlet 103 via air passage 117.

In liquid atomization chamber 101, tubular collision wall 112 open at the top and bottom is provided. Collision wall 112 is fixed inside liquid atomization chamber 101. Furthermore, liquid atomization chamber 101 includes, in the inner area surrounded by collision wall 112, tubular pumping pipe 111 which rotates to draw up (pump up) water. Pumping pipe 111 has a hollow structure in the shape of an inverted cone, and rotary shaft 110 is fixed at the center of the base of the inverted cone in such a manner as to extend in the vertical direction. Rotary shaft 110 is connected to rotary motor 109 provided on the outer surface of liquid atomization chamber 101, and thus the rotary motion of rotary motor 109 is transmitted to pumping pipe 111 through rotary shaft 110, causing pumping pipe 111 to rotate.

As illustrated in FIG. 11, pumping pipe 111 includes a plurality of rotary plates 114 formed so as to protrude outward from the outer surface of pumping pipe 111. The plurality of rotary plates 114 are formed at predetermined intervals along the axis of rotary shaft 110 so as to protrude outward from the outer surface of pumping pipe 111. Rotary plate 114 rotates together with pumping pipe 111 and is therefore preferably in the shape of a horizontal disc that is coaxial with rotary shaft 110. Note that the total number of rotary plates 114 is set, as appropriate, depending on intended performance, the dimensions of pumping pipe 111, and so on.

Furthermore, the wall of pumping pipe 111 includes a plurality of openings 113 penetrating the wall of pumping pipe 111. Each of the plurality of openings 113 is positioned to provide communication between the inside of pumping pipe 111 and an upper surface of rotary plate 114 formed so as to protrude outward from the outer surface of pumping pipe 111. It is necessary to design each opening 113 by setting the size thereof in the circumferential direction (opening percentage) according to the outer diameter of a portion of pumping pipe 111 at which opening 113 is located. For example, it is sufficient that the size of opening 113 in the circumferential direction be set equivalent to 5% to 50% of the outer diameter of pumping pipe 111 and more preferably set equivalent to 5% to 20% of the outer diameter of pumping pipe 111. Note that the dimensions of respective openings 113 may be set equal to one another within this range.

As illustrated in FIG. 10, in a lower portion of liquid atomization chamber 101, reservoir 104 which stores the water to be pumped up by pumping pipe 111 through the pumping port is provided vertically below pumping pipe 111. Reservoir 104 is designed to have a depth such that a lower portion of pumping pipe 111 is partially soaked, for example, a portion the length of which is approximately one-third to one-hundredth of the height of the cone of pumping pipe 111 is soaked. The design for this depth can be adjusted according to a required amount of water to be pumped.

Water is supplied to reservoir 104 using water supply unit 107. A water supply pipe (not illustrated in the drawings) is connected to water supply unit 107 and, for example, water is directly supplied thereto from a water service line by the water supply pipe via a water pressure regulator valve. Note that water supply unit 107 may be configured to supply water to reservoir 104 by drawing up only the required amount of water from a water tank provided outside liquid atomization chamber 101 using the siphon principle in advance. Water supply unit 107 is provided at a position vertically higher than the position of the bottom surface of reservoir 104. Note that water supply unit 107 is preferably provided not only at a higher position than the bottom surface of reservoir 104, but also at a position vertically higher than the position of an upper surface of reservoir 104 (the plane at the highest level of water that can be stored in reservoir 104).

Water level sensor 108 that senses the level of water in reservoir 104 is provided in liquid atomization chamber 101. Water level sensor 108 includes float switch 120. When water in reservoir 104 has not reached a predetermined water level, float switch 120 is OFF, and when water in reservoir 104 reaches the predetermined water level, float switch 120 is turned ON. The predetermined water level is set so that a lower portion of pumping pipe 111 is soaked in the water stored in reservoir 104. When float switch 120 is OFF, water supply unit 107 supplies water to reservoir 104, and when float switch 120 is ON, the water supply from water supply unit 107 to reservoir 104 is stopped. This allows water in reservoir 104 to be maintained at a predetermined water level. Water level sensor 108 is provided at a position vertically higher than the position of the bottom surface of reservoir 104.

Drain pipe 118 is connected to the bottom surface of reservoir 104. A drain port of reservoir 104 that is provided at the position where drain pipe 118 is connected is located at the lowest point of reservoir 104. When the water atomization operation is stopped, a valve (not illustrated in the drawings) provided on drain pipe 118 is opened, and thus water stored in reservoir 104 is drained from drain pipe 118.

Here, the operating principles of water atomization in liquid atomization device 150 will be described. Rotary motor 109 causes rotary shaft 110 to rotate, pumping pipe 111 rotates accordingly, and centrifugal force generated by the rotation allows pumping pipe 111 to draw up the water stored in reservoir 104. The rotational speed of pumping pipe 111 is set to 1,000 to 5,000 rpm. Since pumping pipe 111 has a hollow structure in the shape of an inverted cone, the water drawn up by the rotation is pumped up to the upper portion by moving along the inner wall of pumping pipe 111. Subsequently, the water that has been pumped up is centrifugally discharged from opening 113 of pumping pipe 111 along rotary plate 114 and splashes as water droplets.

Since the kinetic energy of the water splashed from rotary plate 114 decays by friction against air inside collision wall 112, rotary plate 114 is preferably placed as close to collision wall 112 as possible. However, as the distance between collision wall 112 and rotary plate 114 is reduced, the amount of air passing through collision wall 112 is reduced; thus, the lower limit value of the distance between collision wall 112 and rotary plate 114 is arbitrarily determined according to the pressure loss and the amount of air passing through collision wall 112.

Note that the liquid to be atomized may be other than water; for example, a liquid such as antibacterial or deodorant hypochlorous acid water may be used. The atomized hypochlorous acid water is mixed into the air drawn in through inlet 102 of liquid atomization device 150, and then the air is forced out through outlet 103; thus, space in which liquid atomization device 150 is placed can be sterilized or deodorized.

Figure 12:
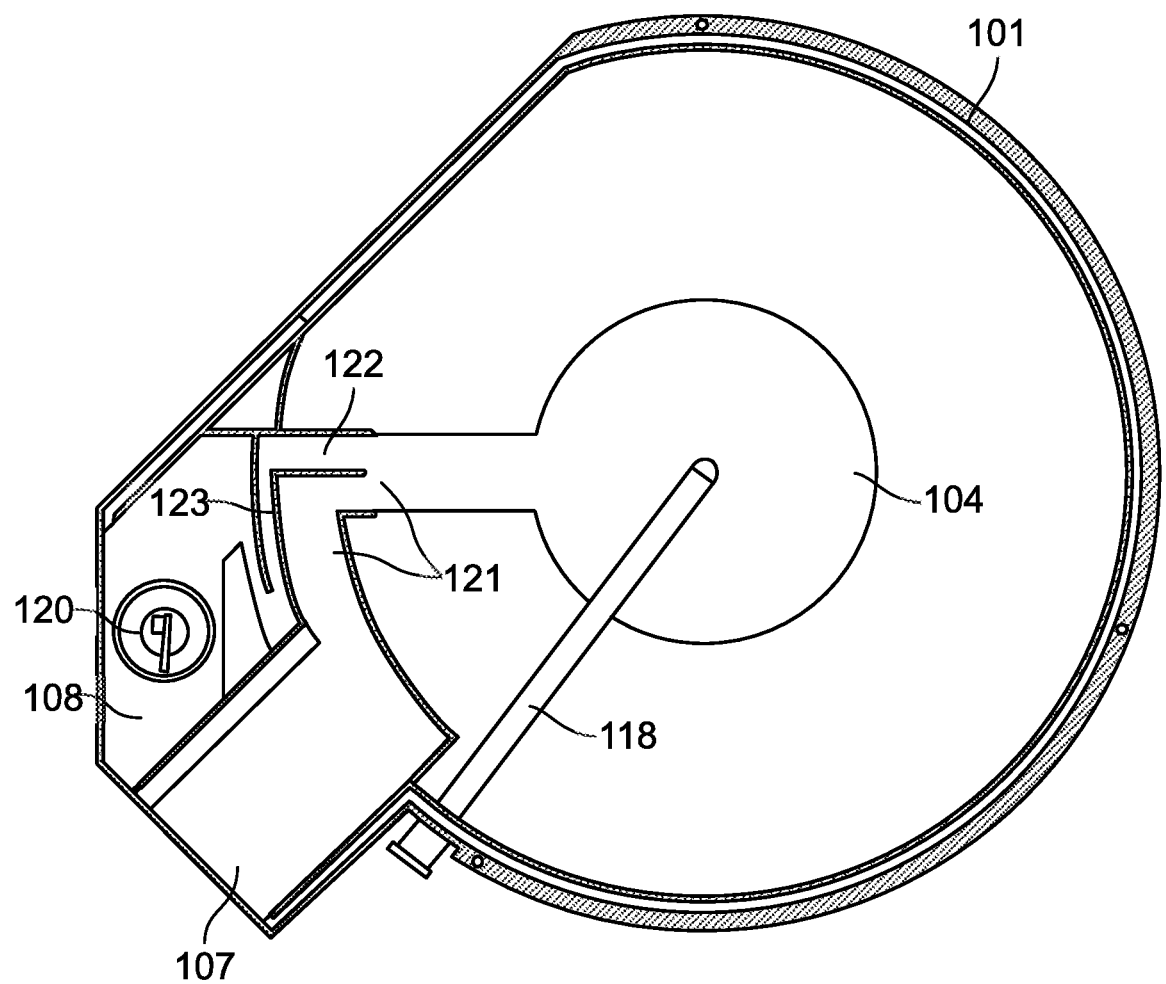
FIG. 12 is a schematic horizontal cross-sectional view of a portion below a collision wall in a liquid atomization chamber according to the third exemplary embodiment of the present disclosure.

FIG. 12 is a schematic horizontal cross-sectional view of a portion below collision wall 112 in liquid atomization chamber 101. Note that illustration of pumping pipe 111 is omitted in FIG. 12.

As illustrated in FIG. 12, first water channel 121 and second water channel 122 are provided in liquid atomization chamber 101. First water channel 121 is a water channel for guiding water to be supplied from water supply unit 107 to reservoir 104. Second water channel 122 is a water channel for providing communication between first water channel 121 and water level sensor 108. In other words, water level sensor 108 is in communication with first water channel 121 via second water channel 122. Furthermore, second water channel 122 includes bent water channel 123 in which the direction of flow of water changes.

Figure 13A:
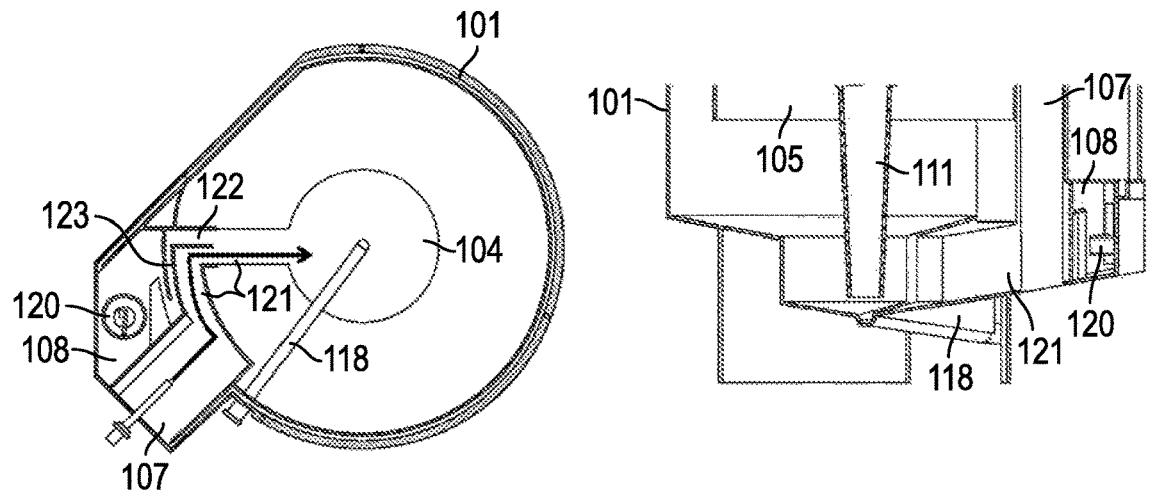
FIG. 13A is a diagram illustrating the movement of water in the case where no water is stored in a reservoir.
Figure 13B:
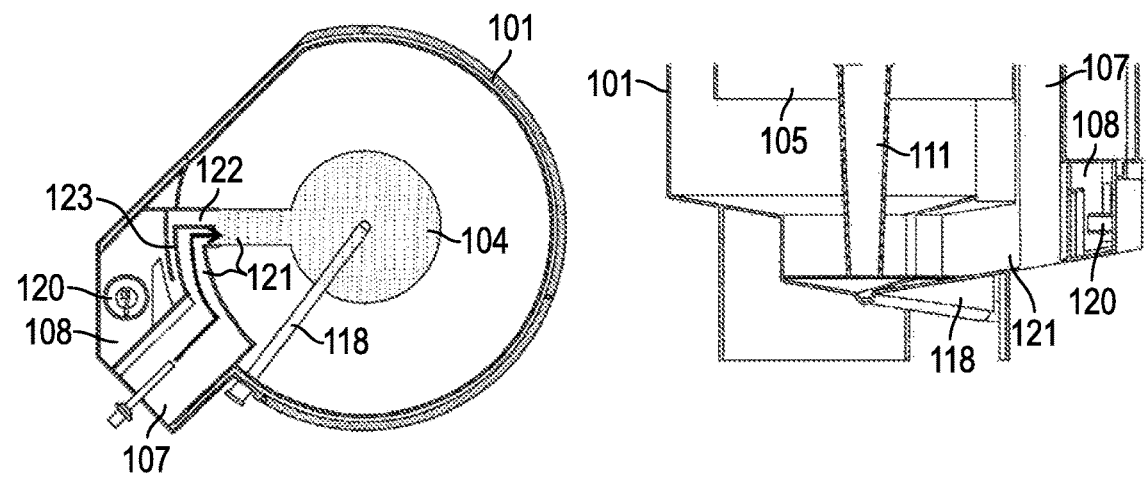
FIG. 13B is a diagram illustrating the movement of water before reaching a predetermined water level that is sensed by a water level sensor.
Figure 13C:
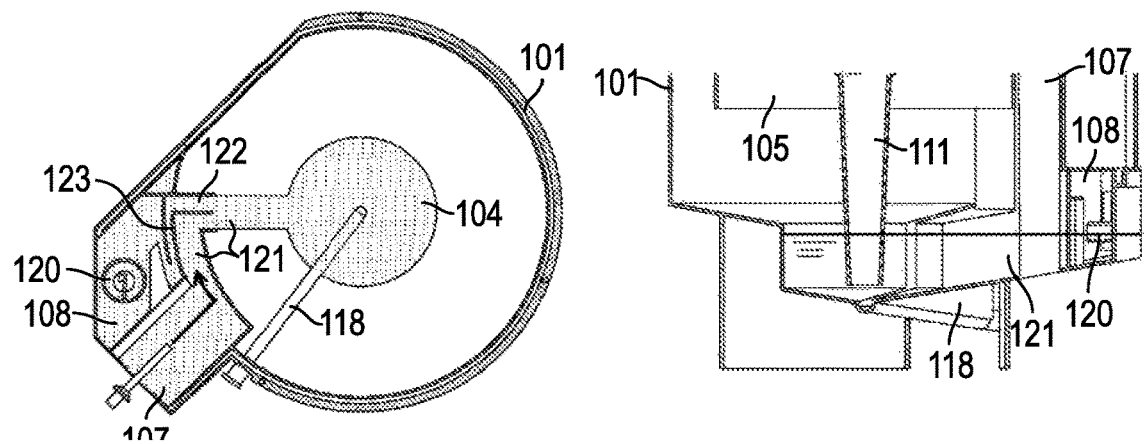
FIG. 13C is a diagram illustrating the movement of water in the case where the predetermined water level is sensed by the water level sensor.

With reference to FIG. 13A, FIG. 13B, and FIG. 13C, the following describes the movement of water in the case where water is supplied to reservoir 104 using water supply unit 107. FIG. 13A is a diagram illustrating the movement of water in the case where no water is stored in reservoir 104. FIG. 13B is a diagram illustrating the movement of water before reaching a predetermined water level that is sensed by water level sensor 108. FIG. 13C is a diagram illustrating the movement of water in the case where the predetermined water level is sensed by water level sensor 108.

As illustrated in FIG. 13A, immediately after water supply unit 107 starts supplying water to reservoir 104, the water supplied from a water supply pipe connected to water supply unit 107 is supplied to reservoir 104 through first water channel 121. Reservoir 104 starts storing the water, and when the level of water increases, first water channel 121 also stores the water corresponding to the water level, as illustrated in FIG. 13B. When the water level further increases, second water channel 122 connected to first water channel 121 also stores the water supplied by water supply unit 107 after passing through reservoir 104, as illustrated in FIG. 13C. The water stored in second water channel 122 enters water level sensor 108 via bent water channel 123.

When the water stored in reservoir 104 reaches a predetermined water level, float switch 120 in water level sensor 108 is turned ON, and water supply unit 107 stops supplying water.

In the case where water supply unit 107 supplies water to reservoir 104, the supplied water temporarily moves to a position away from water supply unit 107 (an inner wall surface of reservoir 104 that faces an exit of first water channel 121). Thus, fluctuations such as a rise of the water surface occur at a position in reservoir 104 that is away from water supply unit 107. To deal with this issue, water level sensor 108 is in communication, via second water channel 122, with first water channel 121 for guiding water from water supply unit 107 to reservoir 104. Specifically, since an entrance of second water channel 122 in communication with water level sensor 108 is located close to the exit of first water channel 121 in communication with water supply unit 107, it is possible to reduce, at water level sensor 108, the impact of a change in the level of the water surface that occurs when water is supplied. Thus, the level of water in reservoir 104 can be accurately sensed.

Water supply unit 107 and water level sensor 108 are provided at positions vertically higher than the position of at least the bottom surface of reservoir 104. Furthermore, as illustrated in FIG. 13A, FIG. 13B, and FIG. 13C, water level sensor 108 is provided at a vertically upper position than the bottom surface of first water channel 121. Thus, even when first water channel 121 and water level sensor 108 are in communication, it is possible to temporarily store, into reservoir 104, water supplied by water supply unit 107, and then as a result of a gradual increase in the water level, fills the space with the water so that the water reaches water level sensor 108 via reservoir 104. This means that the water supplied by water supply unit 107 can be kept from flowing back toward water level sensor 108 before being stored in reservoir 104. Moreover, during the process of water supply from water supply unit 107, water to be supplied from first water channel 121 to reservoir 104 can be reliably kept from flowing back toward water level sensor 108 before being supplied to reservoir 104. Thus, the level of water in reservoir 104 can be accurately sensed. Note that the aforementioned bottom surface of first water channel 121 means a bottom surface portion of the bottom surface of first water channel 121 that is located at the vertically highest position. In the third exemplary embodiment, the bottom surface of first water channel 121 is the water supply unit 107-side bottom surface of first water channel 121.

Furthermore, when water supply unit 107 supplies water to reservoir 104, the force of the water being supplied generates waves in the surface of the water in reservoir 104. In addition, when liquid atomization device 150 operates, waves are also generated in the surface of the water in reservoir 104 by the rotation of pumping pipe 111. Regarding this issue, bent water channel 123 provided in second water channel 122 can suppress propagation of waves generated at the time of the water supply, during operation, etc., in the water flowing from reservoir 104 toward water level sensor 108; therefore, fluctuations in the surface of water in reservoir 104 can be reduced at water level sensor 108. Specifically, with bent water channel 123, waves that are fluctuations in the surface of water generated in reservoir 104 and propagating to second water channel 122 when liquid atomization device 150 is in operation are reflected off a water channel wall surface of bent water channel 123 and thereby change a direction of propagation thereof, and thus direct propagation of the waves to water level sensor 108 can be suppressed. Thus, the level of water in reservoir 104 can be accurately sensed.

Figure 14:
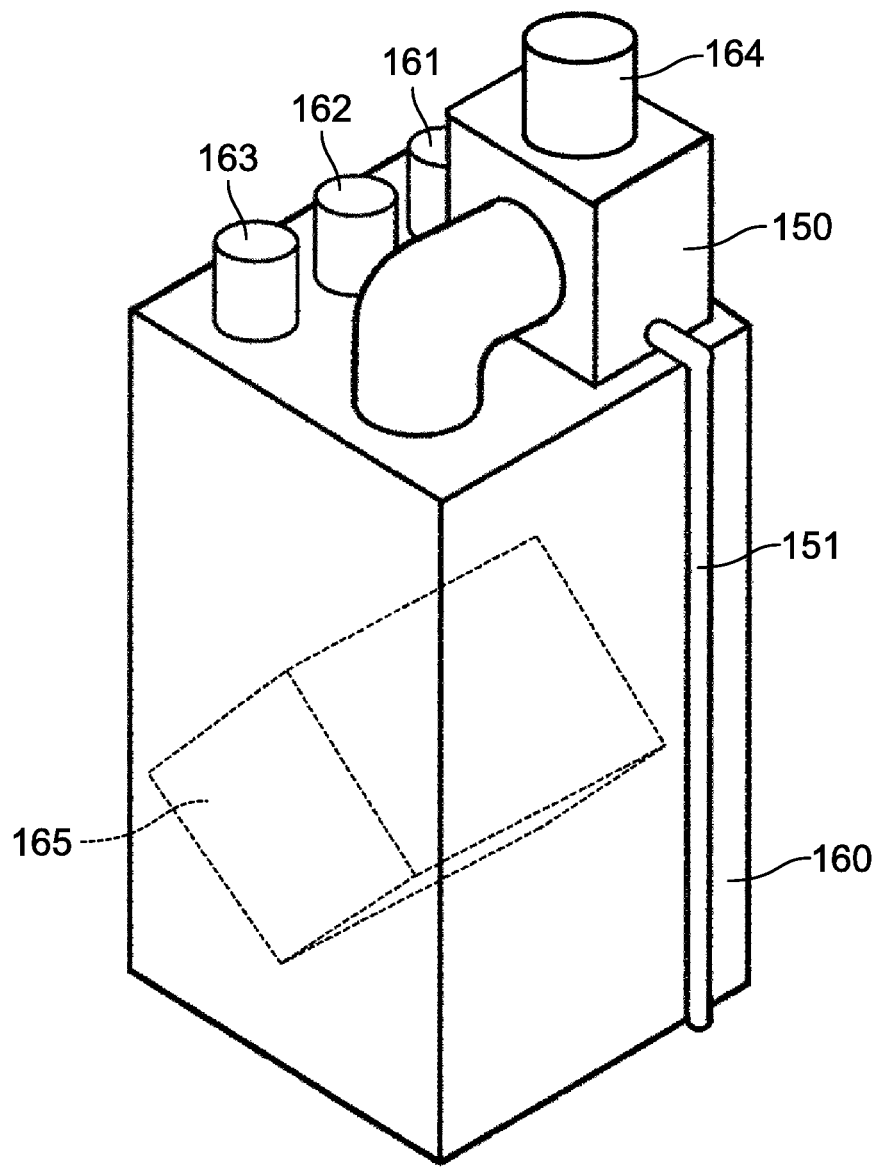
FIG. 14 is a schematic perspective view of a heat exchange ventilation device incorporating the liquid atomization device according to the third exemplary embodiment of the present disclosure.

FIG. 14 is a schematic perspective view of heat exchange ventilation device 160 incorporating liquid atomization device 150 according to the third exemplary embodiment of the present disclosure. Heat exchange ventilation device 160 includes: indoor inlet 161 and air intake port 164 that are provided in a room of a building; exhaust port 162 and outside air inlet 163 that are provided outside the building; and heat exchange element 165 provided in a main body.

Air inside the room is drawn in through indoor inlet 161, and the drawn-in air is discharged to the outside through exhaust port 162. Outside air outside the room is drawn in through outside air inlet 163, and the drawn-in outside air is supplied into the room through air intake port 164. At this time, heat exchange element 165 exchanges heat between the air delivered from indoor inlet 161 to exhaust port 162 and the outside air delivered from outside air inlet 163 to air intake port 164.

Some heat exchange ventilation devices incorporate, as one function, a device that vaporizes a liquid such as a water vaporization device intended to be used to increase humidity and a hypochlorous acid vaporization device intended to be used for sterilization or deodorization. Heat exchange ventilation device 160 incorporates liquid atomization device 150 as the device that vaporizes a liquid. Specifically, liquid atomization device 150 is provided on the air intake port 164 side of heat exchange ventilation device 160. Note that water supply/drain pipe 151 is used to supply water to and drain water from liquid atomization device 150.

Heat exchange ventilation device 160 incorporating liquid atomization device 150 mixes, into outside air that has been subjected to the heat exchange of heat exchange element 165, water or hypochlorous acid water atomized by liquid atomization device 150, and supplies the resultant air into the room through air intake port 164. By using liquid atomization device 150 as a mechanism for vaporizing the liquid, it is possible to obtain miniaturized heat exchange ventilation device 160 with improved energy efficiency.

Liquid atomization device 150 may be provided in an air cleaner or an air conditioner instead of heat exchange ventilation device 160. Some air cleaners or air conditioners incorporate, as one function, a device that vaporizes a liquid such as a water vaporization device intended to be used to increase humidity and a hypochlorous acid vaporization device intended to be used for sterilization or deodorization. By using liquid atomization device 150 as this device, it is possible to obtain a miniaturized air cleaner or air conditioner with improved energy efficiency.

Fourth Exemplary Embodiment

The difference between a liquid atomization device according to the fourth exemplary embodiment and the liquid atomization device according to the third exemplary embodiment is the configuration of water level sensor 108 and a water channel configuration including: first water channel 121 for guiding water from water supply unit 107 to reservoir 104; and second water channel 122 providing communication between first water channel 121 and water level sensor 108. The other configuration of liquid atomization device 150 is substantially the same as that in the third exemplary embodiment. Hereinafter, explanation of the content described in the third exemplary embodiment will be omitted, as appropriate, and the points of difference from the third exemplary embodiment will be mainly explained.

Figure 15:
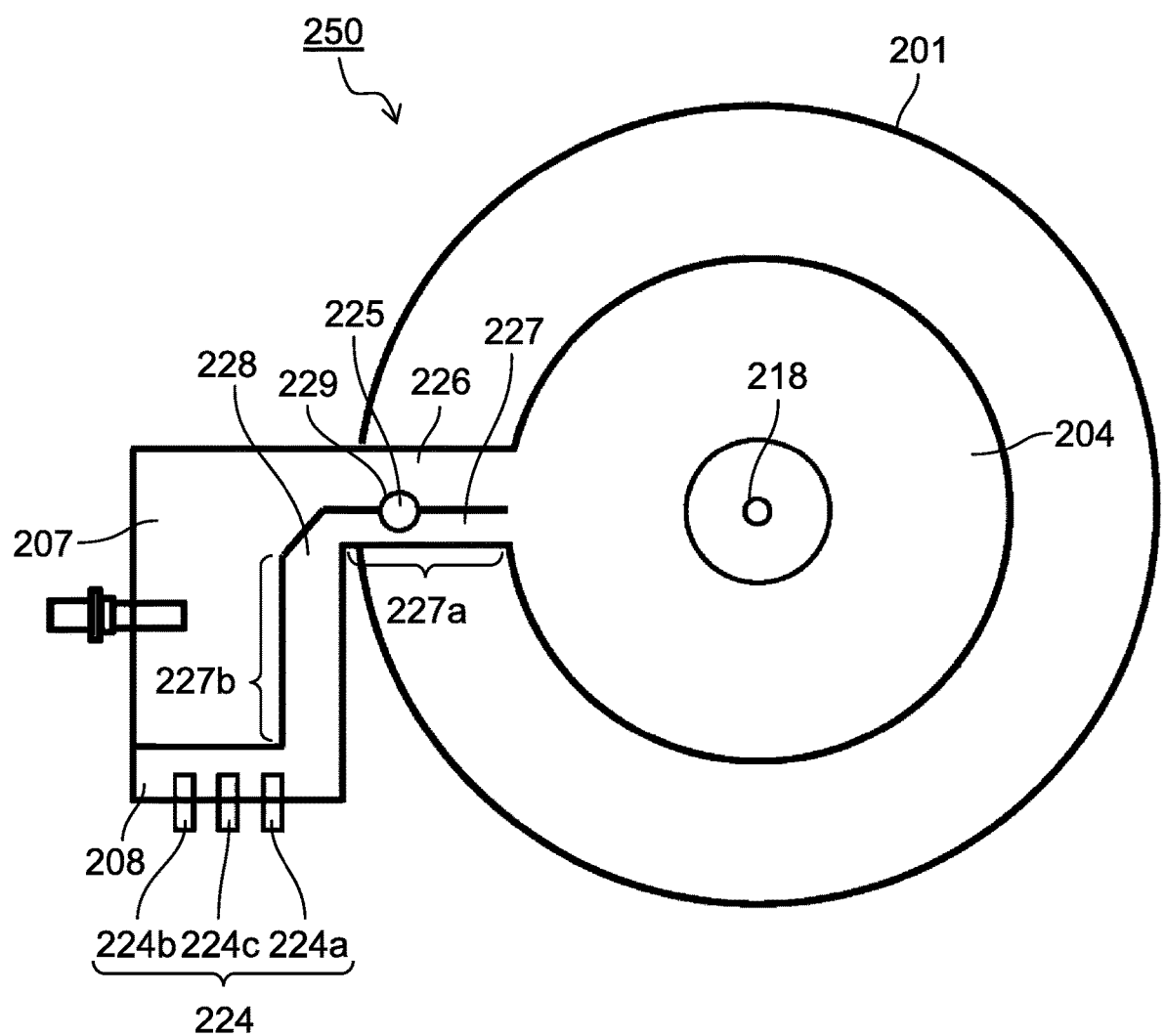
FIG. 15 is a schematic horizontal cross-sectional view of a portion below a collision wall in a liquid atomization device according to the fourth exemplary embodiment of the present disclosure.

With reference to FIG. 15, water level sensor 208 and the water channel configuration (third water channel 226 and fourth water channel 227 to be described later) in liquid atomization device 250 according to the fourth embodiment of the present disclosure will be described. FIG. 15 is a schematic horizontal cross-sectional view of a portion below collision wall 112 in liquid atomization device 250 according to the fourth exemplary embodiment of the present disclosure. Note that although not illustrated in the drawings, water level sensor 208 and water supply unit 207 in liquid atomization device 250 according to the fourth exemplary embodiment are provided at positions vertically higher than the position of the bottom surface of reservoir 204 as in the third exemplary embodiment. Furthermore, water level sensor 208 is provided at a position vertically higher than the position of the bottom surface of third water channel 226 corresponding to first water channel 121 as in the third exemplary embodiment.

First, water level sensor 208 in liquid atomization device 250 according to the fourth exemplary embodiment will be described. Water level sensor 208 according to the fourth exemplary embodiment includes three temperature sensors 224. In this configuration, using two temperature sensors (high-water level sensor 224a and reference sensor 224b) among these temperature sensors, an air temperature and a water temperature are compared, and thus a water level is sensed. High-water level sensor 224a is used to sense that the level of water in reservoir 204 has reached a high-water level, and reference sensor 224b measures the temperature of air in water level sensor 208.

When the level of water in water level sensor 208 has not reached a position at which high-water level sensor 224a is attached (water level detection position), both high-water level sensor 224a and reference sensor 224b detect the temperature of air, and there is no difference in temperature between high-water level sensor 224a and reference sensor 224b. However, when the level of water in water level sensor 208 has increased to the position at which high-water level sensor 224a is attached (water level detection position), high-water level sensor 224a detects the temperature of water, causing a difference in temperature between high-water level sensor 224a and reference sensor 224b. By evaluating whether there is such a difference in temperature, water level sensor 208 detects the level of water.

Furthermore, water level sensor 208 according to the fourth exemplary embodiment is configured to include overflow water level sensor 224c other than two temperature sensors 224 mentioned above. Overflow water level sensor 224c is for detecting an abnormality when the level of water becomes greater than or equal to the high-water level due to some cause. With this, forced drainage from overflow pipe 225 to be described later can be reliably detected.

Regarding the attachment positions of three temperature sensors 224 in water level sensor 208, high-water level sensor 224a, overflow water level sensor 224c, and reference sensor 224b are arranged in order from closest to farthest from reservoir 204, as illustrated in FIG. 15. Furthermore, the order of three temperature sensors 224 from lowest to highest in terms of the attachment height is high-water level sensor 224a, overflow water level sensor 224c, and reference sensor 224b. In other words, the arrangement is oblique when viewed horizontally. With this arrangement, even when a water droplet adhering to each temperature sensor 224 falls, the water droplet is kept from falling on another temperature sensor 224. Thus, it is possible to reduce false detection of temperature sensors 224.

Next, the water channel configuration of liquid atomization device 250 according to the present exemplary embodiment will be described. As illustrated in FIG. 15, third water channel 226 and fourth water channel 227 are provided in liquid atomization chamber 201. Third water channel 226, which corresponds to first water channel 121 according to the third exemplary embodiment, is a water channel for guiding water to be supplied from water supply unit 207 to reservoir 204. Fourth water channel 227, which corresponds to second water channel 122 according to the third exemplary embodiment, is a water channel for providing communication between third water channel 226 and water level sensor 208. In other words, water level sensor 208 is in communication with third water channel 226 via fourth water channel 227.

Fourth water channel 227 includes: reservoir-end water channel 227a in communication with reservoir 204; and water level sensor-end water channel 227b in communication with water level sensor 208. Reservoir-end water channel 227a and water level sensor-end water channel 227b are both in the form of straight lines, are connected so that the orientations thereof are different from each other, and form bent water channel 228 which corresponds to bent water channel 123 according to the third exemplary embodiment. With this, waves that are fluctuations in the surface of water generated in reservoir 204 and propagating to reservoir-end water channel 227a when liquid atomization device 250 is in operation are reflected off a water channel wall surface of bent water channel 228 and thereby change a direction of propagation thereof, and thus direct propagation of the waves to water level sensor 208 can be suppressed.

The water channel width of water level sensor-end water channel 227b is set greater than the water channel width of reservoir-end water channel 227a. Specifically, the water channel width of water level sensor-end water channel 227b is 1.5 to 2.5 times as great as the water channel width of reservoir-end water channel 227a. With this, at the time when the waves that are fluctuations in the surface of water propagating to reservoir-end water channel 227a move from reservoir-end water channel 227a to water level sensor-end water channel 227b, the water channel width increases suddenly, allowing for a reduction in the amplitude of the fluctuations in the level of water. For example, in the case where the water channel width of water level sensor-end water channel 227b is 1.5 times as great as the water channel width of reservoir-end water channel 227a, the amplitude of the waves in water level sensor-end water channel 227b can be controlled under at most two-thirds of the amplitude of the waves in reservoir-end water channel 227a.

Furthermore, in liquid atomization chamber 201, overflow pipe 225 vertically penetrating third water channel 226 and fourth water channel 227 (reservoir-end water channel 227a) is formed. Overflow pipe 225 is formed at a position on the water level sensor 208 side (on the side opposite to reservoir 204) relative to a midpoint of the water channel length of reservoir-end water channel 227a. As a result of providing overflow pipe 225, protrusion 229 protruding in a water channel is formed in reservoir-end water channel 227a, causing a reduction in the water channel width. More specifically, due to protrusion 229, reservoir-end water channel 227a has a reduced water channel width that is in the range of one-half to one-third of the water cannel width of a portion where protrusion 229 is not formed. With this configuration, protrusion 229 can reflect a portion of waves that are fluctuations in the surface of water propagating to reservoir-end water channel 227a, and thus propagation of the waves toward water level sensor 208 can be suppressed.

Overflow pipe 225 is a mechanism which, when the level of water in reservoir 204 becomes greater than or equal to the high-water level due to some cause, forcibly drains water to protect the main body of liquid atomization device 250. Overflow water is drained through overflow pipe 225 connected to drain pipe 218 through which the water in reservoir 204 is drained. Note that overflow pipe 225 is provided vertically slightly above a position at which overflow water level sensor 224c is attached (water level detection position).

As described above, with liquid atomization device 250 according to the fourth exemplary embodiment, as in the third exemplary embodiment, it is possible to suppress propagation of waves generated at the time of the water supply, during operation, etc., in the water flowing from reservoir 204 toward water level sensor 208; therefore, fluctuations in the surface of water in reservoir 204 can be reduced at water level sensor 208. Thus, the level of water in reservoir 204 can be accurately sensed.

Although the present disclosure has been described thus far based on the exemplary embodiments, the present disclosure is not at all limited to the above-described exemplary embodiments, and it can be readily inferred that various improvements and modifications are possible without departing from the principles and spirit of the present disclosure. For instance, the numerical values in the above-described exemplary embodiments are mere examples and, naturally, other numerical values can be applied.

INDUSTRIAL APPLICABILITY

The liquid atomization device according to the present disclosure is applicable to a device that vaporizes a liquid such as a water vaporization device intended to be used to increase humidity and a hypochlorous acid vaporization device intended to be used for sterilization or deodorization. Furthermore, the liquid atomization device according to the present disclosure is applicable to a water vaporization device, a hypochlorous acid vaporization device, or the like incorporated in a heat exchange ventilation device, an air cleaner, and an air conditioner as one function thereof.

REFERENCE MARKS IN THE DRAWINGS 1, 101, 201 liquid atomization chamber
2, 102 inlet
3, 103 outlet
4, 104, 204 reservoir
7, 107, 207 water supply unit
8, 108, 208 water level sensor
9, 109 rotary motor
10, 110 rotary shaft
11, 71, 111 pumping pipe
71a inner wall
12, 112 collision wall
13, 113 opening
14, 114 rotary plate
15, 115 air passage
16, 116 air passage
17, 117 air passage
18, 118, 218 drain pipe
20, 120 float switch
21 pumping port
21a first pumping port
21b second pumping port
22 drain port
23 whirlpool center bottom
24 whirlpool
25 void
26 rib part
50, 150, 250 liquid atomization device
51, 151 water supply/drain pipe
60, 160 heat exchange ventilation device
61, 161 indoor inlet
62, 162 exhaust port
63, 163 outside air inlet
64, 164 air intake port
65, 165 heat exchange element
121 first water channel
122 second water channel
123 bent water channel
226 third water channel
227 fourth water channel
227a reservoir-end water channel
227b water level sensor-end water channel
228 bent water channel
229 protrusion

The invention claimed is:

1. A liquid atomization device, comprising:
an inlet through which air is drawn in;
an outlet through which the air drawn in through the inlet is forced out; and
a liquid atomization chamber in which water is atomized, the liquid atomization chamber being provided in an air passage between the inlet and the outlet, wherein
the liquid atomization chamber includes:
a rotary shaft disposed in a vertical direction, the rotary shaft being rotated by a rotary motor;
a pumping pipe having a tubular shape and including a lower portion having a pumping port and an upper portion fixed to the rotary shaft, the pumping pipe being rotated in coordination with the rotation of the rotary shaft to pump up the water through the pumping port and centrifugally discharge the water that has been pumped up;
a collision wall which the water discharged by the pumping pipe hits to cause atomization of the water;
a reservoir in which the water to be pumped up by the pumping pipe through the pumping port is stored, the reservoir being provided vertically below the pumping pipe; and
a drain port provided on a bottom surface of the reservoir, the drain port being a port through which the water that has been stored is drained, and
the pumping pipe generates, inside the pumping pipe, a whirlpool in the water in the reservoir by the rotation of the pumping pipe, and forms, at a center of the whirlpool, a void providing communication between the pumping port and the drain port.

2. The liquid atomization device according to claim 1, wherein
the pumping pipe includes:
a first pumping port located at a lower position in the pumping pipe;
a second pumping port located above the first pumping port; and
a plurality of rib parts protruding from an inner wall located between the first pumping port and the second pumping port.

3. The liquid atomization device according to claim 1, wherein
when the pumping pipe is viewed from above in the vertical direction, the drain port inward of the pumping port.

4. The liquid atomization device according to claim 1, wherein
when the pumping pipe is viewed from above in the vertical direction, the pumping port and the drain port to overlap each other.

5. The liquid atomization device according to claim 1, wherein
the bottom surface of the reservoir is formed in the shape of a bowl projecting toward the drain port.

6. A liquid atomization device, comprising:
an inlet through which air is drawn in;
an outlet through which the air drawn in through the inlet is forced out; and
a liquid atomization chamber in which water is atomized, the liquid atomization chamber being provided in an air passage between the inlet and the outlet, wherein
the liquid atomization device mixes the water atomized in the liquid atomization chamber into the air drawn in through the inlet, and forces out the air mixed with the water through the outlet,
the liquid atomization chamber includes:
  a pumping pipe having a tubular shape, the pumping pipe being rotated to pump up the water and centrifugally discharge the water that has been pumped up;
  a reservoir in which the water to be pumped up by the pumping pipe is stored, the reservoir being provided vertically below the pumping pipe;
  a water supply unit supplying the water to the reservoir;
  a first water channel guiding the water from the water supply unit to the reservoir; and
  a water level sensor sensing a level of the water in the reservoir,
the water supply unit and the water level sensor are provided at positions vertically higher than a position of a bottom surface of the reservoir,
in an area close to the reservoir, the first water channel is in communication with the water level sensor via a second water channel different from the first water channel, and
when the water is supplied, the water flows from the reservoir toward the water level sensor into the second water channel.

7. The liquid atomization device according to claim 6, wherein
the second water channel includes a bent water channel in which a direction of flow of the water changes.

8. The liquid atomization device according to claim 6, wherein
the water level sensor is provided at a position vertically higher than a position of a bottom surface of the first water channel in an area close to the water supply unit.

9. The liquid atomization device according to claim 7, wherein
the second water channel includes:
  a reservoir-end water channel in communication with the reservoir; and
  a water level sensor-end water channel in communication with the water level sensor, and
a water channel width of the water level sensor-end water channel is set greater than a water channel width of the reservoir-end water channel.

10. The liquid atomization device according to claim 7, wherein
the second water channel includes a protrusion protruding in a water channel and has a reduced water channel width.

11. The liquid atomization device according to claim 1, wherein
the water is hypochlorous acid water.

12. An air cleaner, comprising:
the liquid atomization device according to claim 11.

13. The liquid atomization device according to claim 6, wherein
the water is hypochlorous acid water.

14. An air cleaner, comprising:
the liquid atomization device according to claim 13.

* * * * *